US012770726B2

(12) United States Patent
O'Rourke et al.

(10) Patent No.: US 12,770,726 B2
(45) Date of Patent: Oct. 20, 2026

(54) SYSTEM, METHOD, AND COMPUTER PROGRAM PRODUCT FOR PROVIDING A GATEWAY TO CONNECT A FLUID DELIVERY SYSTEM AND EXTERNAL SYSTEMS

(71) Applicant: BAYER HEALTHCARE LLC, Whippany, NJ (US)

(72) Inventors: Patrick O'Rourke, New Middleton, OH (US); James Hoon Yoo, Baulkham Hills (AU); Jonathan Maton, Princeton Junction, NJ (US); Shahab Taheri, Kleinmachnow (DE); Sung Hoi Park, Bella Vista (AU); Matthew Jay, Auburn (AU); Ruolan Ren, Auburn (AU); Sharon Standish, Pawleys Island, SC (US); Johnnie Ruffin, Jr., North Huntingdon, PA (US); Daryl Huynh, Maastricht (NL)

(73) Assignee: BAYER HEALTHCARE LLC, Whippany, NJ (US)

( * ) Notice: Subject to any disclaimer, the term of this patent is extended or adjusted under 35 U.S.C. 154(b) by 203 days.

(21) Appl. No.: 18/005,199

(22) PCT Filed: Jul. 8, 2021

(86) PCT No.: PCT/US2021/040800

§ 371 (c)(1),
(2) Date: Jan. 12, 2023

(87) PCT Pub. No.: WO2022/015560

PCT Pub. Date: Jan. 20, 2022

(65) Prior Publication Data

US 2023/0268047 A1 Aug. 24, 2023

Related U.S. Application Data

(60) Provisional application No. 63/145,607, filed on May 17, 2021, provisional application No. 63/051,491, filed on Jul. 14, 2020.

(51) Int. Cl.
*G16H 20/17* (2018.01)
*G16H 30/20* (2018.01)
*G16H 40/60* (2018.01)

(52) U.S. Cl.
CPC ............ *G16H 20/17* (2018.01); *G16H 30/20* (2018.01); *G16H 40/60* (2018.01)

(58) Field of Classification Search
CPC ........ G16H 20/17; G16H 30/20; G16H 40/60; G16H 40/40; A61B 6/032; A61B 6/504
(Continued)

(56) References Cited

U.S. PATENT DOCUMENTS 6,643,537 B1 11/2003 Zatezalo et al.
6,970,735 B2 11/2005 Uber, III et al.
(Continued)

FOREIGN PATENT DOCUMENTS

CA 2727784 A1 2/2010
WO WO-2008011401 A2 * 1/2008 ............. A61B 6/481
(Continued)

OTHER PUBLICATIONS

"International Preliminary Report on Patentability from PCT Application No. PCT/US2021/040800", Jan. 26, 2023.

*Primary Examiner* — Peter H Choi
*Assistant Examiner* — Sara Jessica Morice De Vargas
(74) *Attorney, Agent, or Firm* — James R. Stevenson; Steven D. Czajkowski; Joseph L. Kent

(57) ABSTRACT

Provided is a system for enabling communication between a fluid injection system and at least one of a plurality of external systems. The system includes a gateway device and the gateway device includes at least one processor programmed or configured to provide a first communication interface between a hospital information system and a fluid injection system, provide a second communication interface
(Continued)

between a fluid injection system service and control system associated with the fluid injection system and the fluid injection system, and provide a third communication interface between a medical imaging system and the fluid injection system.

28 Claims, 10 Drawing Sheets

(58) Field of Classification Search
USPC .............................................................. 705/2
See application file for complete search history.

(56) References Cited

U.S. PATENT DOCUMENTS

| | | | |
|---|---|---|---|
| 7,094,216 B2 | 8/2006 | Trombley, III et al. | |
| 7,556,619 B2 | 7/2009 | Spohn et al. | |
| 7,996,381 B2 | 8/2011 | Uber, III et al. | |
| 8,147,464 B2 | 4/2012 | Spohn et al. | |
| 8,337,456 B2 | 12/2012 | Schriver et al. | |
| 8,521,716 B2 | 8/2013 | Uber, III et al. | |
| 8,540,698 B2 | 9/2013 | Spohn et al. | |
| 2009/0177050 A1* | 7/2009 | Griffiths | A61B 6/481 600/407 |
| 2014/0172959 A1* | 6/2014 | Hsu | H04L 41/0803 709/203 |
| 2016/0328522 A1 | 11/2016 | Howley | |
| 2016/0331896 A1* | 11/2016 | Nemoto | A61B 6/032 |
| 2018/0075201 A1* | 3/2018 | Davis | G16H 40/63 |
| 2020/0236111 A1* | 7/2020 | Utamaru | G06Q 10/20 |
| 2020/0411176 A1* | 12/2020 | Hadorn | G16H 40/67 |
| 2023/0289168 A1* | 9/2023 | Sethi | G06F 8/65 |

FOREIGN PATENT DOCUMENTS

| | | | | |
|---|---|---|---|---|
| WO | WO-2012154335 A2 * | 11/2012 | A61B 5/0024 |
| WO | WO20120154335 A2 * | 11/2012 | A61B 5/0024 |
| WO | 2017030976 A1 | 2/2017 | |

* cited by examiner

SYSTEM, METHOD, AND COMPUTER PROGRAM PRODUCT FOR PROVIDING A GATEWAY TO CONNECT A FLUID DELIVERY SYSTEM AND EXTERNAL SYSTEMS

CROSS-REFERENCE TO RELATED APPLICATIONS

This application is a U.S. national phase application under 35 U.S.C. § 371 of International Application No. PCT/US2021/040800, filed Jul. 8, 2021, and claims the benefit of U.S. Provisional Patent Application No. 63/051,491, filed Jul. 14, 2020, and U.S. Provisional Application No. 63/145,607, filed May 17, 2021, the entire disclosures of which are hereby incorporated by reference in their entireties.

BACKGROUND

1. Field

This disclosure relates generally to communication systems and/or devices associated with medical devices and, in some non-limiting embodiments, to systems, methods, and computer program products that provide for a gateway that enables communication between a fluid injection system and one or more external systems.

2. Technical Considerations

A fluid injection system (e.g., a medical fluid delivery system) may be used by a medical practitioner, such as a physician, in a medical diagnostic procedure and/or a medical therapeutic procedure. For example, the medical practitioner may use the fluid injection system to inject a patient with one or more medical fluids. The fluid injection system may be used for pressurized injection of a medical fluid, such as a radiological contrast material (e.g., a contrast agent, a radiocontrast agent, contrast media, etc.), and/or a flushing agent, such as saline, in medical imaging procedures, such as angiography, computed tomography (CT), ultrasound, magnetic resonance imaging (MRI), and positron emission tomography (PET). In some instances, the fluid injection system is designed to deliver a preset amount of a medical fluid at a preset flow rate.

In some instances, the fluid injection system may be part of a group of devices that are used in a medical treatment facility, such as a hospital. For example, the fluid injection system may be connected to a medical imaging system, such as a CT scanner and/or an MRI scanner and an information system for the medical treatment facility. In some situations, the fluid injection system and the medical imaging system may communicate information associated with a procedure performed on a patient to the information system via a communication network, and the information system may store the information in an appropriate database so that a medical practitioner may review the information.

SUMMARY

Accordingly, disclosed are systems, methods, and computer program products that provide for a gateway device that enables communication between a fluid injection system and one or more external systems.

Further non-limiting embodiments or aspects are set forth in the following numbered clauses:

Clause 1: A system for enabling communication between a fluid injection system and at least one of a plurality of external systems, comprising: a gateway device, the gateway device comprising: at least one processor programmed or configured to: provide a first communication interface between a hospital information system and a fluid injection system; provide a second communication interface between a fluid injector service and control system associated with the fluid injection system and the fluid injection system; and provide a third communication interface between a medical imaging system and the fluid injection system.

Clause 2: The system of clause 1, wherein the at least one processor is further programmed or configured to: transmit data associated with informatics received from the hospital information system to a fluid injection system via a communications network based on an API call from the fluid injection system.

Clause 3: The system of clause 1 or 2, wherein the at least one processor is further programmed or configured to: receive the data associated with informatics from the hospital information system via the communications network according to a communications protocol for communicating the data associated with informatics.

Clause 4: The system of any of clauses 1-3, wherein, when receiving the data associated with informatics from the hospital information system, the at least one processor is programmed or configured to: receive data associated with a patient procedure from the hospital information system via the communications network according to a Digital Imaging and Communications in Medicine (DICOM) communications protocol.

Clause 5: The system of any of clauses 1-4, wherein, when receiving the data associated with informatics from the hospital information system, the at least one processor is programmed or configured to: receive data associated with an operation of the fluid injection system from the hospital information system via the communications network based on an API call.

Clause 6: The system of any of clauses 1-5, wherein, when receiving the data associated with informatics from the hospital information system, the at least one processor is programmed or configured to: receive data associated with a radiology image from the hospital information system via the communications network according to a Digital Imaging and Communications in Medicine (DICOM) communications protocol.

Clause 7: The system of any of clauses 1-6, wherein, when receiving the data associated with informatics from the hospital information system, the at least one processor is programmed or configured to: receive data associated with a radiology procedure from the hospital information system via the communications network according to a Health Level Seven (HL7) standard communications protocol.

Clause 8: The system of any of clauses 1-7, wherein, when receiving the data associated with informatics from the hospital information system, the at least one processor is programmed or configured to: receive data associated with radiation dosage during a radiology imaging study from the hospital information system via the communications network based on an API call.

Clause 9: The system of any of clauses 1-8, wherein the at least one processor is further programmed or configured to: receive data associated with a service function of the fluid injection system from the fluid injector service and control system via the communications network based on an API call.

Clause 10: The system of any of clauses 1-9, wherein the at least one processor is further programmed or configured to: receive data associated with an operation of the medical imaging system from the medical imaging system via the communications network based on an API call.

Clause 11: The system of any of clauses 1-10, wherein the at least one processor is further programmed or configured to: transmit data associated with service information received from the fluid injector service and control system to the fluid injection system via a communications network based on an API call from the fluid injection system.

Clause 12: The system of any of clauses 1-11, wherein the at least one processor is further programmed or configured to: transmit data associated with an image received from the medical imaging system to the fluid injection system via a communications network based on an API call from the fluid injection system.

Clause 13: The system of any of clauses 1-12, wherein the at least one processor is further programmed or configured to: provide a graphical user interface to a user to receive a user input.

Clause 14: The system of any of clauses 1-13, further comprising a memory device and wherein the memory device stores a plurality of applications, wherein the plurality of applications comprises: an informatics application associated with the first communication interface between the hospital information system and the fluid injection system; a remote service connectivity application associated with the second communication interface between the fluid injector service and control system associated with the fluid injection system and the fluid injection system; and an imaging connectivity system application associated with the third communication interface between the medical imaging system and the fluid injection system.

Clause 15: The system of any of clauses 1-14, further comprising: a display unit; and wherein the plurality of applications comprises: a fourth application associated with a graphical user interface provided to a user by the display unit to receive a user input.

Clause 16: The system of any of clauses 1-15, wherein the gateway device comprises a universal gateway.

Clause 17: A system for enabling communication between a fluid injection system and at least one of a plurality of external systems, comprising: a fluid injection system; and a gateway device, the gateway device comprising: at least one processor programmed or configured to: provide a first communication interface between a hospital information system and the fluid injection system; provide a second communication interface between a fluid injector service and control system associated with the fluid injection system and the fluid injection system; and provide a third communication interface between a medical imaging system and the fluid injection system.

Clause 18: The system of clause 17, wherein the at least one processor is further programmed or configured to: transmit data associated with informatics received from the hospital information system to a fluid injection system via a communications network based on an API call from the fluid injection system.

Clause 19: The system of clause 17 or 18, wherein the at least one processor is further programmed or configured to: receive the data associated with informatics from the hospital information system via the communications network according to a communications protocol for communicating the data associated with informatics.

Clause 20: The system of any of clauses 17-19, wherein, when receiving the data associated with informatics from the hospital information system, the at least one processor is programmed or configured to: receive data associated with a patient procedure from the hospital information system via the communications network according to a Digital Imaging and Communications in Medicine (DICOM) communications protocol.

Clause 21: The system of any of clauses 17-20, wherein, when receiving the data associated with informatics from the hospital information system, the at least one processor is programmed or configured to: receive data associated with an operation of the fluid injection system from the hospital information system via the communications network based on an API call.

Clause 22: The system of any of clauses 17-21, wherein, when receiving the data associated with informatics from the hospital information system, the at least one processor is programmed or configured to: receive data associated with a radiology image from the hospital information system via the communications network according to a Digital Imaging and Communications in Medicine (DICOM) communications protocol.

Clause 23: The system of any of clauses 17-22, wherein, when receiving the data associated with informatics from the hospital information system, the at least one processor is programmed or configured to: receive data associated with a radiology procedure from the hospital information system via the communications network according to a Health Level Seven (HL7) standard communications protocol.

Clause 24: The system of any of clauses 17-23, wherein, when receiving the data associated with informatics from the hospital information system, the at least one processor is programmed or configured to: receive data associated with radiation dosage during a radiology imaging study from the hospital information system via the communications network based on an API call.

Clause 25: The system of any of clauses 17-24, wherein the at least one processor is further programmed or configured to: receive data associated with a service function of the fluid injection system from the fluid injector service and control system via the communications network based on an API call.

Clause 26: The system of any of clauses 17-25, wherein the at least one processor is further programmed or configured to: receive data associated with an operation of the medical imaging system from the medical imaging system via the communications network based on an API call.

Clause 27: The system of any of clauses 17-26, wherein the at least one processor is further programmed or configured to: transmit data associated with service information received from the fluid injector service and control system to the fluid injection system via a communications network based on an API call from the fluid injection system.

Clause 28: The system of any of clauses 17-27, wherein the at least one processor is further programmed or configured to: transmit data associated with an image received from the medical imaging system to the fluid injection system via a communications network based on an API call from the fluid injection system.

Clause 29: The system of any of clauses 17-28, wherein the at least one processor is further programmed or configured to: provide a graphical user interface to a user to receive a user input.

Clause 30: The system of any of clauses 17-29, further comprising a memory device and wherein the memory device stores a plurality of applications, wherein the plurality of applications comprises: an informatics application associated with the first communication interface between the hospital information system and the fluid injection system; a remote service connectivity application associated with the second communication interface between the fluid injector service and control system associated with the fluid injection system and the fluid injection system; and an imaging connectivity system application associated with the third communication interface between the medical imaging system and the fluid injection system.

Clause 31: The system of any of clauses 17-30, further comprising: a display unit; and wherein the plurality of applications comprises: a fourth application associated with a graphical user interface provided to a user by the display unit to receive a user input.

Clause 32: The system of any of clauses 17-31, wherein the gateway device comprises a universal gateway.

Clause 33: A system for enabling communication between a fluid injection system and at least one of a plurality of external systems, comprising: a fluid injection system, the fluid injection system comprising: a gateway device, the gateway device comprising: at least one processor programmed or configured to: provide a first communication interface between a hospital information system and the fluid injection system; provide a second communication interface between a fluid injector service and control system associated with the fluid injection system and the fluid injection system; and provide a third communication interface between a medical imaging system and the fluid injection system.

Clause 34: The system of clause 33, wherein the at least one processor is further programmed or configured to: transmit data associated with informatics received from the hospital information system to a fluid injection system via a communications network based on an API call from the fluid injection system.

Clause 35: The system of clause 33 or 34, wherein the at least one processor is further programmed or configured to: receive the data associated with informatics from the hospital information system via the communications network according to a communications protocol for communicating the data associated with informatics.

Clause 36: The system of any of clauses 33-35, wherein, when receiving the data associated with informatics from the hospital information system, the at least one processor is programmed or configured to: receive data associated with a patient procedure from the hospital information system via the communications network according to a Digital Imaging and Communications in Medicine (DICOM) communications protocol.

Clause 37: The system of any of clauses 33-36, wherein, when receiving the data associated with informatics from the hospital information system, the at least one processor is programmed or configured to: receive data associated with an operation of the fluid injection system from the hospital information system via the communications network based on an API call.

Clause 38: The system of any of clauses 33-37, wherein, when receiving the data associated with informatics from the hospital information system, the at least one processor is programmed or configured to: receive data associated with a radiology image from the hospital information system via the communications network according to a Digital Imaging and Communications in Medicine (DICOM) communications protocol.

Clause 39: The system of any of clauses 33-38, wherein, when receiving the data associated with informatics from the hospital information system, the at least one processor is programmed or configured to: receive data associated with a radiology procedure from the hospital information system via the communications network according to a Health Level Seven (HL7) standard communications protocol.

Clause 40: The system of any of clauses 33-39, wherein, when receiving the data associated with informatics from the hospital information system, the at least one processor is programmed or configured to: receive data associated with radiation dosage during a radiology imaging study from the hospital information system via the communications network based on an API call.

Clause 41: The system of any of clauses 33-40, wherein the at least one processor is further programmed or configured to: receive data associated with a service function of the fluid injection system from the fluid injector service and control system via the communications network based on an API call.

Clause 42: The system of any of clauses 33-41, wherein the at least one processor is further programmed or configured to: receive data associated with an operation of the medical imaging system from the medical imaging system via the communications network based on an API call.

Clause 43: The system of any of clauses 33-42, wherein the at least one processor is further programmed or configured to: transmit data associated with service information received from the fluid injector service and control system to the fluid injection system via a communications network based on an API call from the fluid injection system.

Clause 44: The system of any of clauses 33-43, wherein the at least one processor is further programmed or configured to: transmit data associated with an image received from the medical imaging system to the fluid injection system via a communications network based on an API call from the fluid injection system.

Clause 45: The system of any of clauses 33-44, wherein the at least one processor is further programmed or configured to: provide a graphical user interface to a user to receive a user input.

Clause 46: The system of any of clauses 33-45, further comprising a memory device and wherein the memory device stores a plurality of applications, wherein the plurality of applications comprises: an informatics application associated with the first communication interface between the hospital information system and the fluid injection system; a remote service connectivity application associated with the second communication interface between the fluid injector service and control system associated with the fluid injection system and the fluid injection system; and an imaging connectivity system application associated with the third communication interface between the medical imaging system and the fluid injection system.

Clause 47: The system of any of clauses 33-46, further comprising: a display unit; and wherein the plurality of applications comprises: a fourth application associated with a graphical user interface provided to a user by the display unit to receive a user input.

Clause 48: The system of any of clauses 33-47, wherein the gateway device comprises a universal gateway.

These and other features and characteristics of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the present disclosure. As used in the specification and the claims, the singular form of "a," "an," and "the" include plural referents unless the context clearly dictates otherwise.

BRIEF DESCRIPTION OF THE DRAWINGS

Additional advantages and details of non-limiting embodiments or aspects are explained in greater detail below with reference to the exemplary embodiments that are illustrated in the accompanying schematic figures, in which.

DESCRIPTION

Figure 1:
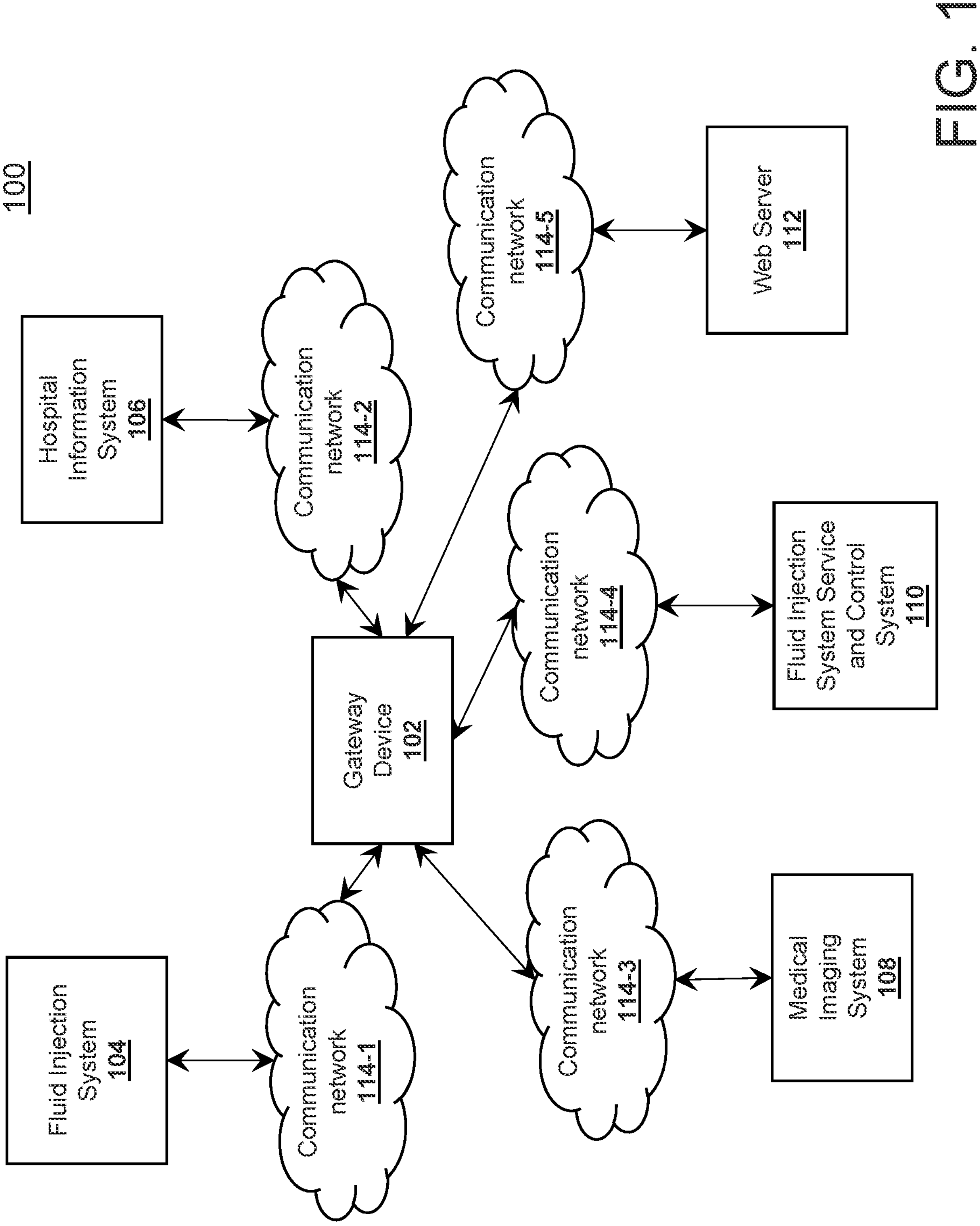
FIG. 1 is a diagram of a non-limiting embodiment of an environment in which systems, methods, and/or computer program products described herein, may be implemented according to the present disclosure.

For purposes of the description hereinafter, the terms "end," "upper," "lower," "right," "left," "vertical," "horizontal," "top," "bottom," "lateral," "longitudinal," and derivatives thereof shall relate to the disclosure as it is oriented in the drawing figures. However, it is to be understood that the disclosure may assume various alternative variations and step sequences, except where expressly specified to the contrary. It is also to be understood that the specific devices and processes illustrated in the attached drawings, and described in the following specification, are simply exemplary embodiments or aspects of the disclosure. Hence, specific dimensions and other physical characteristics related to the embodiments or aspects of the embodiments, disclosed herein, are not to be considered as limiting unless otherwise indicated.

No aspect, component, element, structure, act, step, function, instruction, and/or the like used herein should be construed as critical or essential unless explicitly described as such. Also, as used herein, the articles "a" and "an" are intended to include one or more items and may be used interchangeably with "one or more" and "at least one." Furthermore, as used herein, the term "set" is intended to include one or more items (e.g., related items, unrelated items, a combination of related and unrelated items, and/or the like) and may be used interchangeably with "one or more" or "at least one." Where only one item is intended, the term "one" or similar language is used. Also, as used herein, the terms "has," "have," "having," or the like are intended to be open-ended terms. Further, the phrase "based on" is intended to mean "based at least partially on" unless explicitly stated otherwise.

As used herein, the terms "communication" and "communicate" may refer to the reception, receipt, transmission, transfer, provision, and/or the like of information (e.g., data, signals, messages, instructions, commands, and/or the like). For one unit (e.g., a device, a system, a component of a device or system, combinations thereof, and/or the like) to be in communication with another unit means that the one unit is able to receive information directly or indirectly from and/or transmit information to the other unit. This may refer to a direct or indirect connection that is wired and/or wireless in nature. Additionally, two units may be in communication with each other even though the information transmitted may be modified, processed, relayed, and/or routed between the first and second unit. For example, a first unit may be in communication with a second unit even though the first unit passively receives information and does not actively send information to the second unit. As another example, a first unit may be in communication with a second unit if at least one intermediary unit (e.g., a third unit located between the first unit and the second unit) processes information received from the first unit and sends the processed information to the second unit. In some non-limiting embodiments, information may refer to a network packet (e.g., a data packet and/or the like) that includes data.

In some non-limiting embodiments, a fluid injection system may be connected to a medical imaging system, which itself may be connected to an information system for a medical treatment facility so that information associated with operations of the fluid injection system and/or the medical imaging system may be used by a medical practitioner during treatment of a patient.

However, in order to connect the fluid injection system to the medical imaging system and the information system, the fluid injection system may require complex network communication equipment so that the fluid injection system may communicate with the medical imaging system and the information system efficiently, securely, and without error. Furthermore, the fluid injection system may require specially configured network equipment and/or reprogramming in order to communicate with the medical imaging system and the information system based on a network communication configuration of the medical imaging system and/or the information system.

Systems, methods, and computer program products are disclosed that provide solutions to the above mentioned challenges. For example, as disclosed herein, a system for enabling communication between a fluid injection system and at least one of a plurality of external systems may include a gateway device that includes at least one processor programmed or configured to provide a first communication interface between a hospital information system and a fluid injection system, provide a second communication interface between a fluid injector system service and control system associated with the fluid injection system and the fluid injection system, and provide a third communication interface between a medical imaging system and the fluid injection system. In this way, the system may eliminate the need for complex network communication equipment as part of, or in addition to, the fluid injection system. Furthermore, such a system may reduce the amount of network resources consumed based on updating and/or configuring the fluid injection system in order to connect the fluid injection system with the medical imaging system and/or the hospital information system.

Referring now to FIG. 1, FIG. 1 is a diagram of a non-limiting embodiment of an environment 100 in which devices, systems, methods, and/or computer program products, described herein, may be implemented. As shown in FIG. 1, environment 100 includes gateway device 102, fluid injection system 104, and a plurality of external systems, such as hospital information system 106, medical imaging system 108, fluid injection system service and control system 110, and web server 112. Gateway device 102 may interconnect (e.g., establish a connection to communicate with and/or the like) fluid injection system 104, hospital information system 106, medical imaging system 108, fluid injection system service and control system 110, and/or and web server 112 via communication networks 114-1, 114-2, 114-3, 114-4, and 114-5 (referred to individually as communication network 114 or plural as communication networks 114, unless otherwise noted). In some non-limiting embodiments, gateway device 102 may interconnect (e.g., establish a connection to communicate with and/or the like) fluid injection system 104, hospital information system 106, medical imaging system 108, fluid injection system service and control system 110, and/or web server 112 via wired connections, wireless connections, or a combination of wired and wireless connections.

In some non-limiting embodiments, gateway device 102 may include one or more devices capable of being in communication with fluid injection system 104, hospital information system 106, medical imaging system 108, fluid injection system service and control system 110, and/or web server 112 via communication network 114. For example, gateway device 102 may include a telecommunications gateway (e.g., a network gateway), a universal gateway, and/or other like devices. Additionally or alternatively, gateway device 102 may include one or more computing devices, such as one or more desktop computers, one or mobile devices (e.g., one or more tablets, one or more smartphones, etc.), one or more servers, and/or the like. In some non-limiting embodiments, gateway device 102 may include one or more (e.g., a plurality of) applications (e.g., software applications) that perform a set of functionalities on an external application programming interface (API) that allows fluid injection system 104 to send data to an external system associated with the external API and to receive data from the external system associated with the external API. In one example, gateway device 102 may provide the ability to download an application, such as a Bayer S/W application, to gateway device 102 (e.g., a mobile device of gateway device 102, which provides a Bring Your Own Device operability). In some non-limiting embodiments, the application may be supported by an application associated with fluid injection system 104 that would allow gateway device 102 (e.g., a mobile device of gateway device 102), which may function as a control room display, to be the only one device that controls fluid injection system 104 and, in such an example, gateway device 102 may provide an authentication function. In some non-limiting embodiments, gateway device 102 may be able to access a network resource, such as a uniform resource locator (URL), to determine applications (e.g., services of applications) that are available to gateway device 102 and gateway device 102 and/or fluid injection system 104 may download one or more applications via gateway device 102.

In some non-limiting embodiments, fluid injection system 104 may include one or more devices capable of being in communication with gateway device 102, hospital information system 106, medical imaging system 108, fluid injection system service and control system 110, and/or web server 112 via communication network 114 and be capable of performing fluid injection procedures. For example, fluid injection system 104 may include one or more fluid injectors capable of communicating via communication network 114 and capable of performing fluid injection procedures involving a radiological contrast material (e.g., a contrast agent, a radiocontrast agent, contrast media, etc.), such as iodinated based contrast media and/or gadolinium based contrast media.

In some non-limiting embodiments, fluid injection system 104 includes one or more injection devices (e.g., one or more fluid injection devices). In some non-limiting embodiments, fluid injection system 104 is configured to administer (e.g., inject, deliver, etc.) contrast fluid including a contrast agent to a patient, and/or administer an aqueous fluid, such as saline, to a patient before, during, and/or after administering the contrast fluid. For example, fluid injection system 104 can inject one or more prescribed dosages of contrast fluid directly into a patient's blood stream via a hypodermic needle and syringe. In some non-limiting embodiments, fluid injection system 104 may be configured to continually administer the aqueous fluid to a patient through a peripheral intravenous line (PIV) and catheter, and one or more prescribed dosages of contrast fluid may be introduced into the PIV and administered via the catheter to the patient. In some non-limiting embodiments, fluid injection system 104 is configured to inject a dose of contrast fluid followed by administration of a particular volume of the aqueous fluid. In some non-limiting embodiments, fluid injection system 104 may include one or more exemplary injection systems or injectors that are disclosed in: U.S. patent application Ser. No. 09/715,330, filed on Nov. 17, 2000, issued as U.S. Pat. No. 6,643,537; U.S. patent application Ser. No. 09/982,518, filed on Oct. 18, 2001, issued as U.S. Pat. No. 7,094,216; U.S. patent application Ser. No. 10/825,866, filed on Apr. 16, 2004, issued as U.S. Pat. No. 7,556,619; U.S. patent application Ser. No. 12/437,011, filed May 7, 2009, issued as U.S. Pat. No. 8,337,456; U.S. patent application Ser. No. 12/476, 513, filed Jun. 2, 2009, issued as U.S. Pat. No. 8,147,464; and U.S. patent application Ser. No. 11/004,670, filed on Dec. 3, 2004, issued as U.S. Pat. No. 8,540,698, the disclosures of each of which are incorporated herein by reference in their entireties. In some non-limiting embodiments, fluid injection system 104 may include the MEDRAD® Stellant CT Injection System, the MEDRAD® Stellant Flex CT Injection System, the MEDRAD® MRXperion MR Injection System, the MEDRAD® Mark 7 Arterion Injection System, the MEDRAD® Intego PET Infusion System, or the MEDRAD® Centargo CT Injection System, all of which are provided by Bayer Healthcare LLC.

In some non-limiting embodiments, hospital information system 106 may include one or more devices capable of being in communication with gateway device 102, fluid injection system 104, medical imaging system 108, and fluid injection system service and control system 110 via communication network 114. For example, hospital information system 106 may include one or more computing devices, such as one or more desktop computers, one or mobile devices, one or more servers, and/or the like. In some non-limiting embodiments, hospital information system 106 may include one or more subsystems, such as a patient procedure tracking system (e.g., a system that operates a modality worklist, a system that provides patient demographic information for fluid injection procedures and/or medical imaging procedures, etc.), a fluid injector management system, an image archive and communication system (e.g., a picture archive and communication system (PACS)), a radiology information system, and/or a radiology analytics system (e.g., the Radimetrics Enterprise Application marketed and sold by Bayer HealthCare LLC).

In some non-limiting embodiments, medical imaging system 108 may include one or more devices capable of being in communication with gateway device 102, fluid injection system 104, hospital information system 106, fluid injection system service and control system 110, and/or web server 112 via communication network 114. For example, medical imaging system 108 may include one or more scanners, such as a CT scanner and/or an MRI scanner, capable of communicating via communication network 114 and capable of performing medical imaging procedures involving the use of a radiological contrast material.

In some non-limiting embodiments, fluid injection system service and control system 110 may include one or more devices capable of being in communication with gateway device 102, fluid injection system 104, hospital information system 106, medical imaging system 108, and/or web server 112 via communication network 114. For example, fluid injection system service and control system 110 may include one or more computing devices, such as one or more desktop computers, one or mobile devices, one or more servers, and/or the like. In some non-limiting embodiments, fluid injection system service and control system 110 may provide the functionality for a user (e.g., a service representative) to interact with fluid injection system 104 and/or gateway device 102 for maintenance purposes. For example, fluid injection system service and control system 110 may provide the functionality for the user to perform upgrades, perform restoration operations, logging operations, data backup operations, and/or the like. In some non-limiting embodiments, fluid injection system service and control system 110 may be a subsystem of hospital information system 106 and fluid injection system service and control system 110 may communicate with gateway device 102 via communication network 114-4.

In some non-limiting embodiments, fluid injection system service and control system 110 may include a back-end system associated with gateway device 102 and/or fluid injection system 104. In some non-limiting embodiments, fluid injection system service and control system 110 may include a cloud computing system that stores data in an associated database. In some non-limiting embodiments, fluid injection system service and control system 110 may be capable of interacting with fluid injection system 104 to provide functionality, such as remote equipment service for fluid injection system 104 (e.g., VirtualCARE® Remote Support service for injection systems and devices provided by Bayer HealthCare LLC). In some non-limiting embodiments, fluid injection system service and control system 110 may be operated by or on behalf of an original equipment manufacturer (OEM) of fluid injection system 104 (e.g., an OEM of one or more components or devices of fluid injection system 104), a provider of fluid injection system 104, an imaging site or a hospital in which fluid injection system 104 is operated, a service technician assigned to fluid injection system 104, and/or the like.

In some non-limiting embodiments, web server 112 may include one or more devices capable of being in communication with gateway device 102, fluid injection system 104, hospital information system 106, medical imaging system 108, and/or fluid injection system service and control system 110 via communication network 114. For example, web server 112 may include one or more computing devices, such as one or more servers and/or the like. In some non-limiting embodiments, web server 112 may provide a web-based user interface to gateway device 102 that allows for control of and/or access to functionality of fluid injection system 104. In some non-limiting embodiments, web server 112 may receive requests via a network protocol (e.g., HTTP, HTTPS, etc.) for a network resource and transmit the content of the network resource and/or a message regarding the network resource (e.g., an error message).

In some non-limiting embodiments, communication network 114 (e.g., one or more of communication networks 114-1, 114-2, 114-3, 114-4, and 114-5) may include one or more wired and/or wireless networks. For example, communication network 114 may include a cellular network (e.g., a long-term evolution (LTE) network, a third generation (3G) network, a fourth generation (4G) network, a fifth generation (5G) network, a code division multiple access (CDMA) network, and/or the like), a local area network (LAN), a wide area network (WAN), a wireless LAN (WLAN), a private network, an ad hoc network, an intranet, the Internet, a fiber optic-based network, an Ethernet network, a universal serial bus (USB) network, a cloud computing network, and/or the like, and/or a combination of some or all of these or other types of networks.

The number and arrangement of systems and/or devices shown in FIG. 1 are provided as an example. There may be additional systems and/or devices, fewer systems and/or devices, different systems and/or devices, or differently arranged systems and/or devices than those shown in FIG. 1. Furthermore, two or more systems and/or devices shown in FIG. 1 may be implemented within a single system or a single device, or a single system or a single device shown in FIG. 1 may be implemented as multiple, distributed systems or devices. Additionally or alternatively, a set of systems or a set of devices (e.g., one or more systems, one or more devices) of environment 100 may perform one or more functions described as being performed by another set of systems or another set of devices of environment 100.

Figure 2:
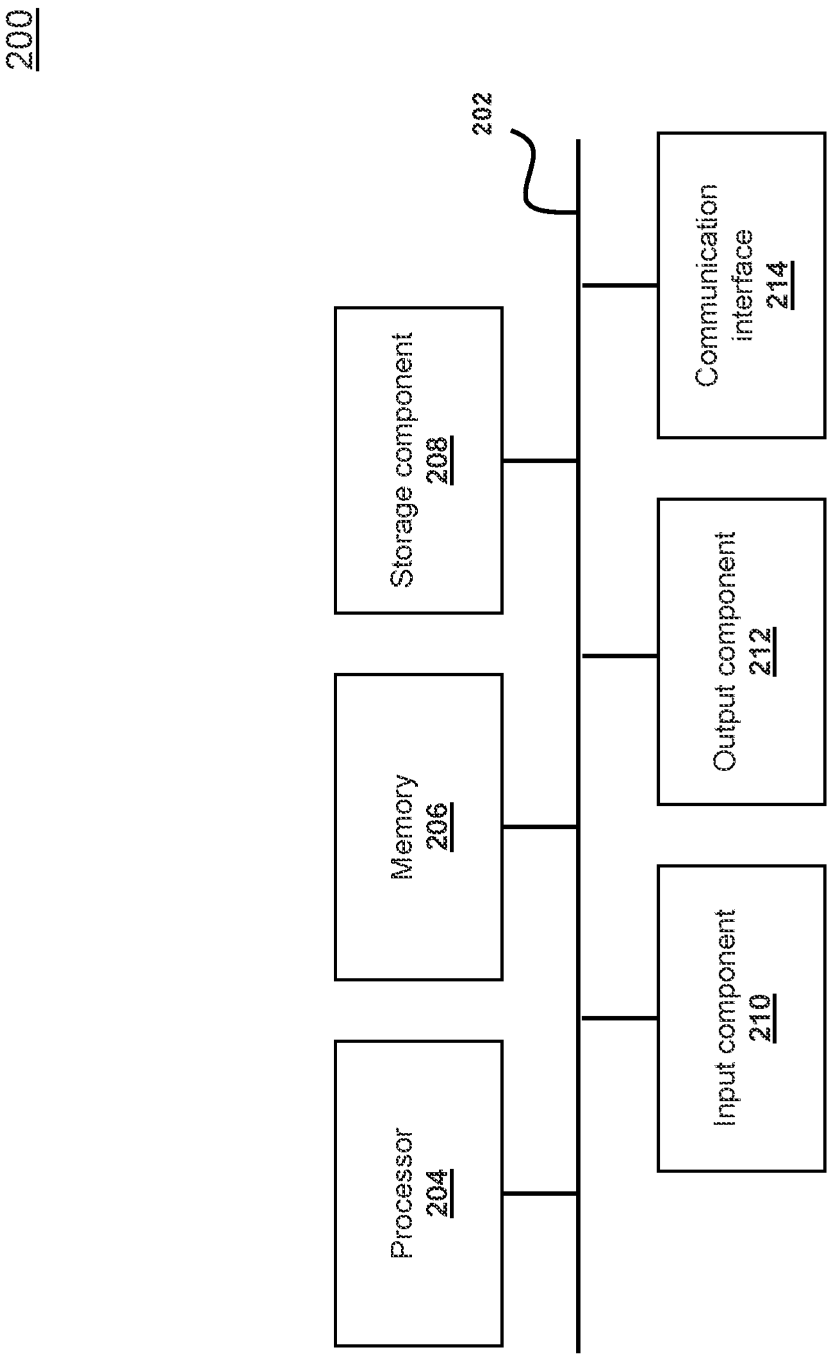
FIG. 2 is a diagram of a non-limiting embodiment of components of one or more devices and/or one or more systems of FIG. 1.

Referring now to FIG. 2, FIG. 2 is a diagram of example components of device 200. Device 200 may correspond to gateway device 102, fluid injection system 104, hospital information system 106, medical imaging system 108, fluid injection system service and control system 110, and/or web server 112. In some non-limiting aspects or embodiments, gateway device 102, fluid injection system 104, hospital information system 106, medical imaging system 108, fluid injection system service and control system 110, and/or web server 112 may include at least one device 200 and/or at least one component of device 200. As shown in FIG. 2, device 200 may include bus 202, processor 204, memory 206, storage component 208, input component 210, output component 212, and communication component 214.

Bus 202 may include a component that permits communication among the components of device 200. In some non-limiting embodiments or aspects, processor 204 may be implemented in hardware, software, or a combination of hardware and software. For example, processor 204 may include a processor (e.g., a central processing unit (CPU), a graphics processing unit (GPU), an accelerated processing unit (APU), and/or the like), a microprocessor, a digital signal processor (DSP), and/or any processing component (e.g., a field-programmable gate array (FPGA), an application-specific integrated circuit (ASIC), and/or the like) that can be programmed to perform a function. Memory 206 may include random access memory (RAM), read-only memory (ROM), and/or another type of dynamic or static storage device (e.g., flash memory, magnetic memory, optical memory, and/or the like) that stores information and/or instructions for use by processor 204.

Storage component 208 may store information and/or software related to the operation and use of device 200. For example, storage component 208 may include a hard disk (e.g., a magnetic disk, an optical disk, a magneto-optic disk, a solid state disk, and/or the like), a compact disc (CD), a digital versatile disc (DVD), a floppy disk, a cartridge, a magnetic tape, and/or another type of computer-readable medium, along with a corresponding drive.

Input component 210 may include a component that permits device 200 to receive information, such as via user input (e.g., a touchscreen display, a keyboard, a keypad, a mouse, a button, a switch, a microphone, a camera, and/or the like). Additionally or alternatively, input component 210 may include a sensor for sensing information (e.g., a global positioning system (GPS) component, an accelerometer, a gyroscope, an actuator, and/or the like). Output component 212 may include a component that provides output information from device 200 (e.g., a display, a speaker, one or more light-emitting diodes (LEDs), and/or the like).

Communication component 214 may include a transceiver-like component (e.g., a transceiver, a separate receiver and transmitter, and/or the like) that enables device 200 to communicate with other devices, such as via a wired connection, a wireless connection, or a combination of wired and wireless connections. Communication component 214 may permit device 200 to receive information from another device and/or provide information to another device. For example, communication component 214 may include an Ethernet interface, an optical interface, a coaxial interface, an infrared interface, a radio frequency (RF) interface, a universal serial bus (USB) interface, a WiFi® interface, a cellular network interface, and/or the like.

Device 200 may perform one or more processes described herein. Device 200 may perform these processes based on processor 204 executing software instructions stored on a computer-readable medium, such as memory 206 and/or storage component 208. A computer-readable medium (e.g., a non-transitory computer-readable medium) is defined herein as a non-transitory memory device. A non-transitory memory device includes memory space located inside of a single physical storage device or memory space spread across multiple physical storage devices.

Software instructions may be read into memory 206 and/or storage component 208 from another computer-readable medium or from another device via communication component 214. When executed, software instructions stored in memory 206 and/or storage component 208 may cause processor 204 to perform one or more processes described herein. Additionally or alternatively, hardwired circuitry may be used in place of or in combination with software instructions to perform one or more processes described herein. Thus, embodiments or aspects described herein are not limited to any specific combination of hardware circuitry and software.

Memory 206 and/or storage component 208 may include data storage or one or more data structures (e.g., a database and/or the like). Device 200 may be capable of retrieving information from, storing information in, or searching information stored in the data storage or one or more data structures in memory 206 and/or storage component 208.

The number and arrangement of components shown in FIG. 2 are provided as an example. In some non-limiting embodiments or aspects, device 200 may include additional components, fewer components, different components, or differently arranged components than those shown in FIG. 2. Additionally or alternatively, a set of components (e.g., one or more components) of device 200 may perform one or more functions described herein as being performed by another set of components of device 200.

Figure 3:
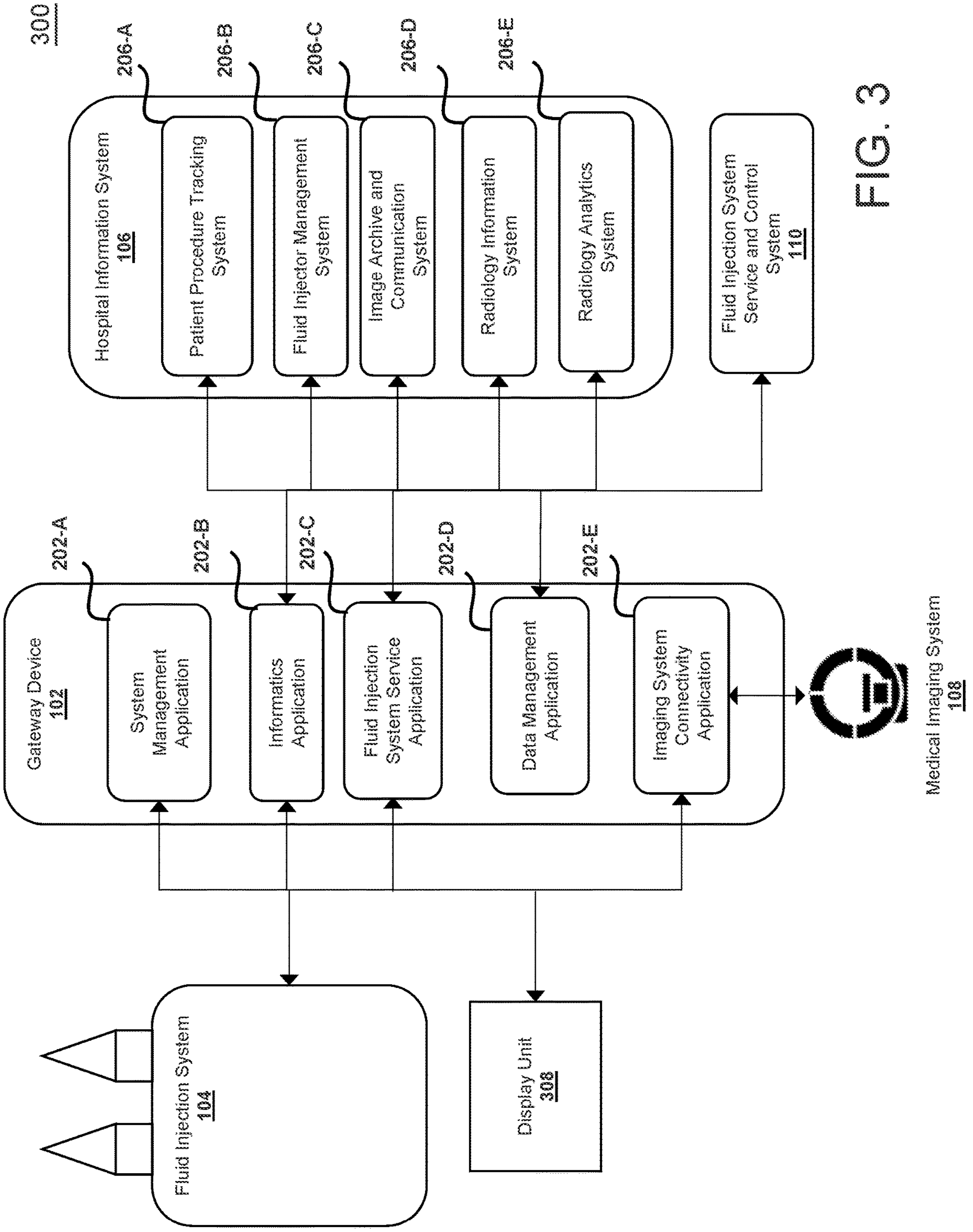
FIG. 3 is a diagram of a non-limiting embodiment of a system for enabling communication between a fluid injection system and at least one of a plurality of external systems.
Figure 4:
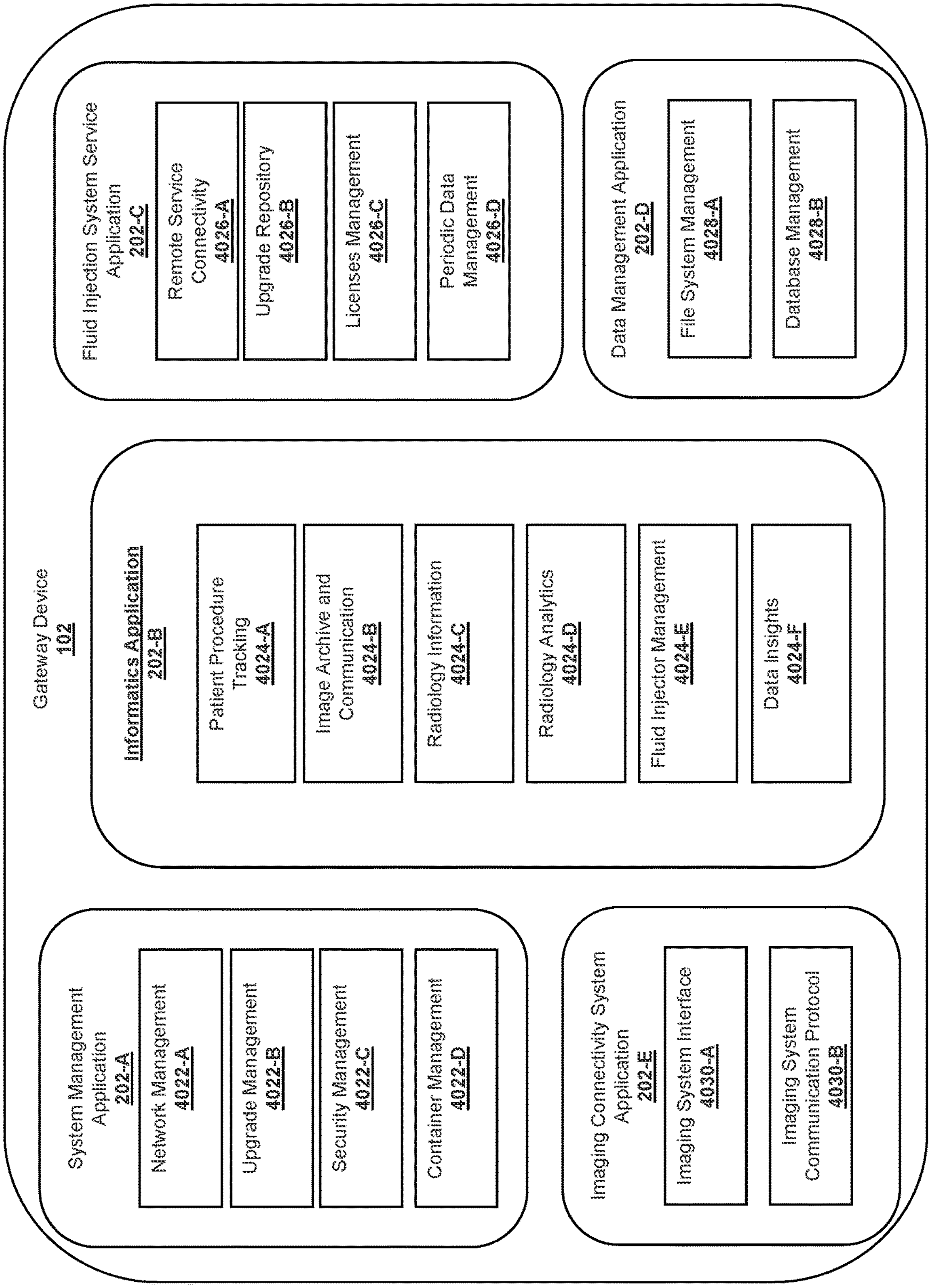
FIG. 4 is a diagram of a non-limiting embodiment of applications of a gateway device.

Referring now to FIGS. 3 and 4, FIG. 3 is a diagram of a non-limiting embodiment of a system 300 for enabling communication between a fluid injection system and at least one of a plurality of external systems. In some non-limiting embodiments or aspects, one or more of the functions described herein with respect to system 300 may be performed (e.g., completely, partially, and/or the like) by gateway device 102. In some non-limiting embodiments, one or more of the functions described with respect to system 300 may be performed (e.g., completely, partially, and/or the like) by another device or a group of devices separate from and/or including gateway device 102, such as fluid injection system 104, hospital information system 106, medical imaging system 108, fluid injection system service and control system 110, and/or display unit 308. FIG. 4 is a diagram of a non-limiting embodiment of applications of gateway device 102.

As shown in FIGS. 3 and 4, gateway device 102 may include a plurality of applications, such as system management application 202-A, informatics application 202-B, fluid injection system service application 202-C, data management application 202-D, and imaging system connectivity application 202-E. In some non-limiting embodiments, the plurality of applications may be stored in a memory device of gateway device 102. In some non-limiting embodiments, each of the plurality of applications may be associated with an API associated with a respective application (e.g., a first API associated with a first application, a second API associated with a second application, a third API associated with a third application, etc.) that allows fluid injection system 104 to interface (e.g., communicate, establish a communication interface, etc.) with gateway device 102 and/or that allows gateway device 102 to interface with hospital information system 106 (e.g., individual subsystems of hospital information system 106, such as patient procedure tracking system 206-A, fluid injector management system 206-B, image archive and communication system 206-C, radiology information system 206-D, and/or radiology analytics system 206-E).

In some non-limiting embodiments, each application of the plurality of applications may include a common software platform application that provides common features and functionality that are mutual of all fluid injection system modalities. In this way, gateway device 102 may be able to interface with a fluid injection system without regard to a specific manufacturer of the fluid injection system.

In some non-limiting embodiments, system management application 202-A may provide operational control of aspects of gateway device 102. For example, system management application 202-A may provide management of operational control of informatics application 202-B, fluid injection system service application 202-C, data management application 202-D, and/or imaging system connectivity application 202-E. In some non-limiting embodiments, system management application 202-A may provide a user interface (e.g., a web-based user interface) that allows a user to control fluid injection system 104. For example, a user may be able to initiate medical imaging, fluid injection, and/or other additional procedures to be performed by fluid injection system 104 via the user interface. Additionally or alternatively, the user interface may allow the user to control aspects of informatics application 202-B, fluid injection system service application 202-C, data management application 202-D, and/or imaging system connectivity application 202-E.

As further shown in FIG. 3, system 300 may include display unit 308. In some non-limiting embodiments, display unit 308 may be capable of displaying the user interface (e.g., the web-based user interface) provided by system management application 202-A. In some non-limiting embodiments, display unit 308 may include a computing device, such as a smart display unit, a portable computer, such as a tablet, a laptop, and/or the like. In some non-limiting embodiments, display unit 308 may include a touchscreen for receiving inputs by a user.

In some non-limiting embodiments, informatics application 202-B may be associated with a first communication interface of gateway device 102 between hospital information system 106 and fluid injection system 104. For example, gateway device 102 may provide the first communication interface between hospital information system 106 and fluid injection system 104 based on informatics application 202-B. In some non-limiting embodiments, a communication interface may include a set of communication settings (e.g., protocols, standards, etc.) that enables one device (e.g., one device of a system) to telecommunicate with another device. In some non-limiting embodiments, informatics application 202-B may provide functionality for fluid injection system 104 to interact with hospital information system 106 (e.g., any of the plurality of subsystems of hospital information system 106). Additionally or alternatively, informatics application 202-B may provide for storage of data for fluid injection system 104.

In some non-limiting embodiments, fluid injection system service application 202-C may be associated with a second communication interface of gateway device 102 between fluid injector service and control system 110 and fluid injection system 104. For example, gateway device 102 may provide the second communication interface between fluid injector service and control system 110 associated with fluid injection system 104 and fluid injection system 104. In some non-limiting embodiments, fluid injection system service application 202-C may provide functionality for a user (e.g., a service representative) to interact with fluid injection system 104 and/or gateway device 102 to perform maintenance operations.

In some non-limiting embodiments, data management application 202-D may be associated with a third communication interface of gateway device 102 between hospital information system 106 and fluid injection system 104. For example, gateway device 102 may provide the third communication interface between hospital information system 106 and fluid injection system 104. In some non-limiting embodiments, the third communication interface may be, or may be the same as or similar to, the first communication interface between hospital information system 106 and fluid injection system 104. In some non-limiting embodiments, data management application 202-D may provide functionality associated with file system and database management for gateway device 102. Additionally or alternatively, data management application 202-D may provide for operational control regarding storage of data for fluid injection system 104.

In some non-limiting embodiments, imaging system connectivity application 202-E may be associated with a fourth communication interface of gateway device 102 between medical imaging system 108 and fluid injection system 104. For example, gateway device 102 may provide the fourth communication interface between medical imaging system 108 and fluid injection system 104. In some non-limiting embodiments, system management application 202-A may be associated with the fourth interface of gateway device 102 between a user and fluid injection system 104 and/or gateway device 102. In some non-limiting embodiments, imaging system connectivity application 202-E may provide functionality for fluid injection system 104 to interact with medical imaging system 108. In some non-limiting embodiments, imaging system connectivity application 202-E may abstract an interface of medical imaging system 108 (e.g., an ISI interface, an ISI2 interface, and/or a Connect CT interface) to a standard format for fluid injection system 104 to utilize.

In some non-limiting embodiments, gateway device 102 may provide the first communication interface between hospital information system 106 and fluid injection system 104 such that informatics application 202-B provides the ability for fluid injection system 104 to receive data based on an API call from fluid injection system 104 to gateway device 102. In some non-limiting embodiments, gateway device 102 may transmit data associated with informatics received from hospital information system 106 to fluid injection system 104 via a communication network 114. For example, gateway device 102 may transmit data associated with informatics received from hospital information system 106 to fluid injection system 104 via communication network 114 based on an API call to informatics application 202-B from the fluid injection system. Data associated with informatics may include data associated with identification of a patient, data associated with a patient examination procedure (e.g., a fluid injection procedure and a medical imaging procedure performed on a patient), such as data associated with a contrast fluid provided during a fluid injection procedure, a gauge of a catheter used during a fluid injection procedure, and a fluid injection protocol for a fluid injection procedure. In some non-limiting embodiments, gateway device 102 may store data associated with a patient examination procedure and/or data associated with a configuration of fluid injection system 104 with informatics application 202-B.

As further shown in FIG. 3, hospital information system 106 may include a plurality of subsystems. The plurality of subsystems may include patient procedure tracking system 206-A, fluid injector management system 206-B, image archive and communication system 206-C, radiology information system 206-D, and radiology analytics system 206-E.

In some non-limiting embodiments, gateway device 102 may receive the data associated with informatics from hospital information system 106 via communication network 114, according to a communications protocol for communicating the data associated with informatics. For example, gateway device 102 may receive data associated with a patient procedure from hospital information system 106 (e.g., from patient procedure tracking system 206-A) via communication network 114 (e.g., communication network 114-2) according to a Digital Imaging and Communications in Medicine (DICOM) communications protocol, data associated with an operation of the fluid injection system from hospital information system 106 (e.g., from fluid injector management system 206-B) via communication network 114 based on an API call (e.g., an API call from gateway device 102 to fluid injector management system 206-B), data associated with a radiology image from hospital information system 106 (e.g., from image archive and communication system 206-C) via communication network 114 according to a DICOM communications protocol, data associated with a patient examination procedure from hospital information system 106 (e.g., from radiology information system 206-D) via communication network 114 according to a Health Level Seven (HL7) standard communications protocol, and/or data associated with radiation dosage during a medical imaging procedure from hospital information system 106 (e.g., from radiology analytics system 206-E) via communication network 114 based on an API call (e.g., an API call from gateway device 102 to radiology analytics system 206-E).

In some non-limiting embodiments, gateway device 102 may provide the second communication interface between fluid injection system service and control system 110 and fluid injection system 104, such that fluid injection system service application 202-C provides the ability for fluid injection system 104 to receive data based on an API call from fluid injection system 104 to gateway device 102. In some non-limiting embodiments, gateway device 102 may transmit data associated with service information received from fluid injection system service and control system 110 to fluid injection system 104 via communication network 114. For example, gateway device 102 may transmit data associated with service information received from fluid injection system service and control system 110 to fluid injection system 104 via communication network 114 based on an API call to fluid injection system service application 202-C from fluid injection system 104. In some non-limiting embodiments, gateway device 102 may receive data associated with a service function of fluid injection system 104 from fluid injection system service and control system 110 via communication network 114 (e.g., communication network 114-4 or communication network 114-2) based on an API call (e.g., an API call from gateway device 102 to fluid injection system service and control system 110).

In some non-limiting embodiments, gateway device 102 may provide the third communication interface between medical imaging system 108 and fluid injection system 104, such that imaging system connectivity application 202-E provides the ability for fluid injection system 104 to receive data based on an API call from fluid injection system 104 to gateway device 102. In some non-limiting embodiments, gateway device 102 may transmit data associated with an image received from medical imaging system 108 to fluid injection system 104 via communication network 114. For example, gateway device 102 may transmit data associated with the image received from medical imaging system 108 to fluid injection system 104 via communication network 114 based on an API call to imaging system connectivity application 202-E from fluid injection system 104. In some non-limiting embodiments, gateway device 102 may transmit data associated with a fluid injection procedure (e.g., data associated with an amount of time for injecting a radiological contrast material into a patient) received from fluid injection system 104 to medical imaging system 108 via communication network 114. For example, gateway device 102 may transmit the data associated with the fluid injection procedure received from fluid injection system 104 to medical imaging system 108 via communication network 114 based on an API call (e.g., an API call for an imaging system interface (ISI), an API call for an ISI2 interface, an API call for a Connect CT interface, etc.) to imaging system connectivity application 202-E from medical imaging system 108. In some non-limiting embodiments, medical imaging system 108 may perform a medical imaging procedure on a patient based on the data associated with the fluid injection procedure. In some non-limiting embodiments, gateway device 102 may receive data associated with an operation of medical imaging system 108 from medical imaging system 108 via communication network 114 (e.g., communication network 114-3) based on an API call (e.g., an API call from gateway device 102 to medical imaging system 108).

In some non-limiting embodiments, gateway device 102 may provide the fourth interface to a user to receive a user input, such that system management application 202-A may provide the ability for gateway device 102 to receive the user input from the user. In some non-limiting embodiments, the fourth interface is a graphical user interface. In some non-limiting embodiments, gateway device 102 may provide the fourth interface to the user (e.g., an administrator) to configure communication networks 114, the plurality of applications stored on gateway device 102, and/or an operating system of gateway device 102. In some non-limiting embodiments, gateway device 102 may provide the fourth interface to allow the user to manage a configuration (e.g., provide control functionality, adjust settings for communication, such as device addresses, communication protocols, etc.) of an API associated with an application stored on gateway device 102. In some non-limiting embodiments, system management application 202-A provides an API that allows fluid injection system 104 to interface with high-level functionality of gateway device 102. For example, gateway device 102 may provide access to high-level functionality of gateway device 102 based on an API call to system management application 202-A from fluid injection system 104. In some non-limiting embodiments, system management application 202-A may provide a GUI for a user (e.g., an administrator) to configure one or more of communication networks 114, manage users of gateway device 102, control updates for the OS and applications of gateway device 102, and/or monitor applications of gateway device 102.

As further shown in FIG. 4, each application of the plurality of applications of gateway device 102 may provide services (e.g., additional software or hardware functionality, such as micro-services, features, etc.) associated with each application. In some non-limiting embodiments, system management application 202-A may include network management service 4022-A, upgrade management service 4022-B, security management service 4022-C, and/or container management service 4022-D. In some non-limiting embodiments, network management service 4022-A may provide for functionality associated with control of communications via communication network 114. For example, network management service 4022-A may provide for control of network addresses, communication protocols, and/or the like. In some non-limiting embodiments, upgrade management service 4022-B may provide for functionality associated with control of upgrades to be made with regarding to applications and/or services of gateway device 102. For example, upgrade management service 4022-B may provide for control regarding upgrades to be made to services of informatics application 202-B. In some non-limiting embodiments, security management service 4022-C may provide for functionality associated with control of access to gateway device 102. For example, security management service 4022-C may provide for control regarding users that are able to access gateway device 102, authentication methods for access to gateway device 102, and/or the like. In some non-limiting embodiments, container management service 4022-D may provide for functionality associated with control of services, which may be structured as containers, provided by informatics application 202-B.

In some non-limiting embodiments, informatics application 202-B may include patient procedure tracking service 4024-A, image archive and communication service 4024-B, radiology information service 4024-C, radiology analytics service 4024-D, fluid injector management service 4024-E, and/or data insights service 4024-F. In some non-limiting embodiments, patient procedure tracking service 4024-A may provide for functionality associated with tracking patient procedures that are to be performed by fluid injection system 104 (e.g., functionality associated with patient demographic information for fluid injection procedures and/or medical imaging procedures). For example, patient procedure tracking service 4024-A may provide for reporting, alerts, messaging, and/or the like with regard to timing of patient procedures. In some non-limiting embodiments, image archive and communication service 4024-B may provide for functionality associated with images (e.g., images provided by medical imaging techniques, scans, scanned images, etc.) received during a fluid injection procedure and/or medical imaging procedure. For example, image archive and communication service 4024-B may provide for receiving, storing, accessing, transmitting and/or the like, with regard to images. In some non-limiting embodiments, radiology information service 4024-C may provide for functionality associated with records of medical imaging procedures. In some non-limiting embodiments, radiology information service 4024-C may provide for patient scheduling, resource management, examination performance tracking, reporting, results distribution, and/or procedure billing with regard to medical imaging procedures. In some non-limiting embodiments, radiology analytics service 4024-D may provide for functionality associated with metrics for medical imaging procedures (e.g., a radiological imaging procedure, a radiology imaging study). For example, radiology analytics service 4024-D may provide for reporting, tracking, alerts, messaging, and/or the like with regard to information associated with a medical imaging procedure, such as data associated with dosage of radiation and/or contrast fluid, information with regard to procedure protocol management, and/or information with regard to benchmarking. In some non-limiting embodiments, fluid injector management service 4024-E may provide for functionality associated with control and/or management of injection protocols for fluid injection systems. For example, fluid injector management service 4024-E may provide for receiving, storing, transmitting, and/or otherwise managing fluid injection systems and/or fluid injection protocols used by the fluid injection systems. In some non-limiting embodiments, data insights service 4024-F may provide for functionality associated with insights to be gained from data associated with fluid injection and/or medical imaging procedures. For example, data insights service 4024-F may provide for reporting, tracking, alerts, messaging, and/or the like with regard to equipment (e.g., medical supplies used during procedures, including contrast fluid, intravenous catheters, etc.) and/or services used during medical imaging procedures.

In some non-limiting embodiments, informatics application 202-B of gateway device 102 may provide for cloud network storage of data associated with (e.g., received via, stored via, transmitted via, etc.) patient procedure tracking service 4024-A, image archive and communication service 4024-B, radiology information service 4024-C, radiology analytics service 4024-D, fluid injector management service 4024-E, and/or data insights service 4024-F. In this way, gateway device 102 may provide for the collection, storage, and access of data associated with informatics application 202-B that reduces the need for resources (e.g., memory resources, network resources, etc.) to be available on fluid injection system 104. In some non-limiting embodiments, machine learning techniques may be applied to the data associated with patient procedure tracking service 4024-A, image archive and communication service 4024-B, radiology information service 4024-C, radiology analytics service 4024-D, fluid injector management service 4024-E, and/or data insights service 4024-F that is collected and stored in cloud network storage. For example, machine learning techniques may be applied to data associated with patients (e.g., patient demographics), data associated with a fluid injection system, data associated with a medical imaging system, data associated with a contrast fluid, data associated with a catheter used during a fluid injection procedure, and/or the like, and the output of the machine learning techniques may include recommendations for fluid injection procedure protocols.

In some non-limiting embodiments, the services of informatics application 202-B may be subscription based and require users to sign up for terms and conditions. In some non-limiting embodiments, levels of services may be provided based on a subscription associated with patient procedure tracking service 4024-A, image archive and communication service 4024-B, radiology information service 4024-C, radiology analytics service 4024-D, fluid injector management service 4024-E, and/or data insights service 4024-F. For example, gateway device 102 may provide access to one or more of patient procedure tracking service 4024-A, image archive and communication service 4024-B, radiology information service 4024-C, radiology analytics service 4024-D, fluid injector management service 4024-E, and data insights service 4024-F based on a level of service that a user subscribes to.

In some non-limiting embodiments, fluid injection system service application 202-C may include remote service connectivity service 4026-A, upgrade repository service 4026-B, licenses management service 4026-C, and/or periodic data management service 4026-D. In some non-limiting embodiments, remote service connectivity service 4026-A may provide for functionality associated with connectivity for maintenance and/or repair of fluid injection system 104. For example, remote service connectivity service 4026-A may provide for access to and/or control of diagnostic operations of fluid injection system 104 by a remote service technician. In some non-limiting embodiments, upgrade repository service 4026-B may provide for functionality associated with upgrades (e.g., executable files associated with upgrades) to services of gateway device 102 and/or fluid injection system 104. For example, upgrade repository service 4026-B may provide for receiving, storing, accessing, and/or the like with regard to records regarding upgrades for services of gateway device 102 and/or fluid injection system 104. In some non-limiting embodiments, licenses management service 4026-C may provide for functionality associated with licenses to services of gateway device 102 and/or fluid injection system 104. For example, licenses management service 4026-C may provide for receiving, storing, accessing, and/or the like with regard to records regarding licenses for services of gateway device 102 and/or fluid injection system 104. In some non-limiting embodiments, periodic data management service 4026-D may provide for functionality associated with management of time sensitive data associated with gateway device 102 and/or fluid injection system 104. For example, periodic data management service 4026-D may provide for reporting, tracking, alerts, messaging, and/or the like with regard to time sensitive data associated with gateway device 102 and/or fluid injection system 104. In some non-limiting embodiments, time sensitive data associated with gateway device 102 and/or fluid injection system 104 may include backups of data associated with procedure protocols, data associated with examination records, data associated with configuration files, and/or the like.

In some non-limiting embodiments, data management application 202-D may include file system management service 4028-A and/or database management service 4028-B. In some non-limiting embodiments, file system management service 4028-A may provide for functionality associated with management of a file system of gateway device 102. In some non-limiting embodiments, database management service 4028-B may provide for functionality associated with management of one or more databases associated with gateway device 102.

In some non-limiting embodiments, imaging connectivity system application 202-E may include imaging system interface service 4030-A and/or imaging system communication protocol service 4030-B. In some non-limiting embodiments, imaging system interface service 4030-A may provide functionality associated with communication (e.g., communication based on controller area network (CAN) technology) between medical imaging system 108 and fluid injection system 104. For example, imaging system interface service 4030-A may provide for a user interface of medical imaging system 108 (e.g., an ISI interface, an ISI2 interface, a Connect CT interface, etc.) to be generated in a standard format for fluid injection system 104 to utilize. In some non-limiting embodiments, imaging system communication protocol service 4030-B may provide functionality associated with communication between medical imaging system 108 and fluid injection system 104 in addition to (e.g., complimentary to) or independent of (e.g., separate from, instead of) imaging system interface service 4030-A. For example, imaging system communication protocol service 4030-B may provide for communication between medical imaging system 108 and fluid injection system 104 based on a communication protocol that is different from a communication protocol used by imaging system interface service 4030-A.

In some non-limiting embodiments, gateway device 102 may provide a user interface (e.g., a web-based user interface) for control of fluid injection system 104 and medical imaging system 108. In this way, gateway device 102 may eliminate the need for separate control units (e.g., separate computing devices that are specifically designed for control of fluid injection system 104 and medical imaging system 108, such as separate workstations) for each of fluid injection system 104 and medical imaging system 108 to control fluid injection system 104 and medical imaging system 108.

Figure 5:
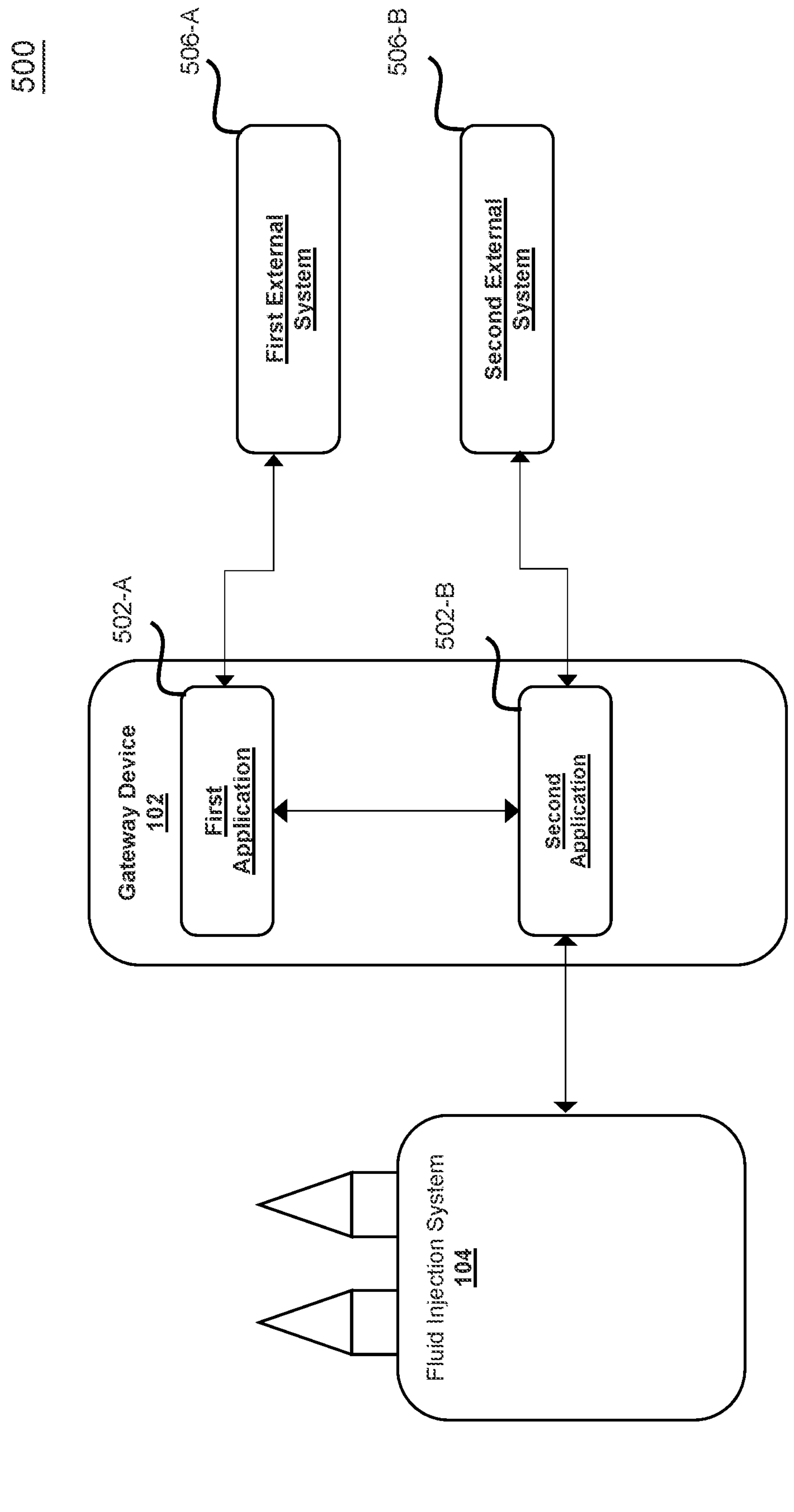
FIG. 5 is a diagram of a non-limiting embodiment of an implementation of a system for enabling communication between a fluid injection system and at least one of a plurality of external systems.

Referring now to FIG. 5, FIG. 5 is a diagram of a non-limiting embodiment of a system 500 for enabling communication between a fluid injection system and at least one of a plurality of external systems. In some non-limiting embodiments or aspects, one or more of the functions described herein with respect to system 500 may be performed (e.g., completely, partially, and/or the like) by gateway device 102. In some non-limiting embodiments, one or more of the functions described herein with respect to system 500 may be performed (e.g., completely, partially, and/or the like) by another device or a group of devices separate from and/or including gateway device 102, such as fluid injection system 104, hospital information system 106, medical imaging system 108, fluid injection system service and control system 110, and/or web server 112.

As shown in FIG. 5, first application 502-A (e.g., one of system management application 202-A, informatics application 202-B, fluid injection system service application 202-C, data management application 202-D, or imaging system connectivity application 202-E) and second application 502-B (e.g., another one of system management application 202-A, informatics application 202-B, fluid injection system service application 202-C, data management application 202-D, or imaging system connectivity application 202-E) may be stored on gateway device 102. As further shown in FIG. 5, first application 502-A may correspond to first external system 506-A (e.g., one of hospital information system 106, one of a plurality of subsystems of hospital information system 106, such as patient procedure tracking system 206-A, fluid injector management system 206-B, image archive and communication system 206-C, radiology information system 206-D, radiology analytics system 206-E, medical imaging system 108, or fluid injection system service and control system 110) and second application 502-B may correspond to second external system 506-B (e.g., another one of hospital information system 106, one of a plurality of subsystems of hospital information system 106, such as patient procedure tracking system 206-A, fluid injector management system 206-B, image archive and communication system 206-C, radiology information system 206-D, radiology analytics system 206-E, medical imaging system 108, or fluid injection system service and control system 110).

In some non-limiting embodiments, fluid injection system 104 may interact with gateway device 102 based on first application 502-A and second application 502-B, and gateway device 102 may interact with first external system 506-A and/or second external system 506-B as described herein. In some non-limiting embodiments, first application 502-A and second application 502-B may interact. For example, second application 502-B may interface with first application 502-A based on an API call from second application 502-B to first application 502-A. In some non-limiting embodiments, second external system 506-B may interface with second application 502-B and second application 502-B may interface with fluid injection system 104. For example, second external system 506-B may provide data to second application 502-B and second application 502-B may receive data from first application 502-A based on the API call from second application 502-B to first application 502-A. Fluid injection system 104 may receive data from second application 502-B (e.g., based on an API call from fluid injection system 104 to second application 502-B) that includes data from second external system 506-B and data from first application 502-A (e.g., data that is aggregated from the data from second external system 506-B and the data from first application 502-A) based on the API call from second application 502-B to first application 502-A. In this way, gateway device 102 may reduce an amount of network resources that are consumed when obtaining data from an external system and data from an application stored on gateway device 102 and providing the data to fluid injection system 104 as compared to a situation in which fluid injection system 104 would obtain separate data from two external systems.

Figure 6:
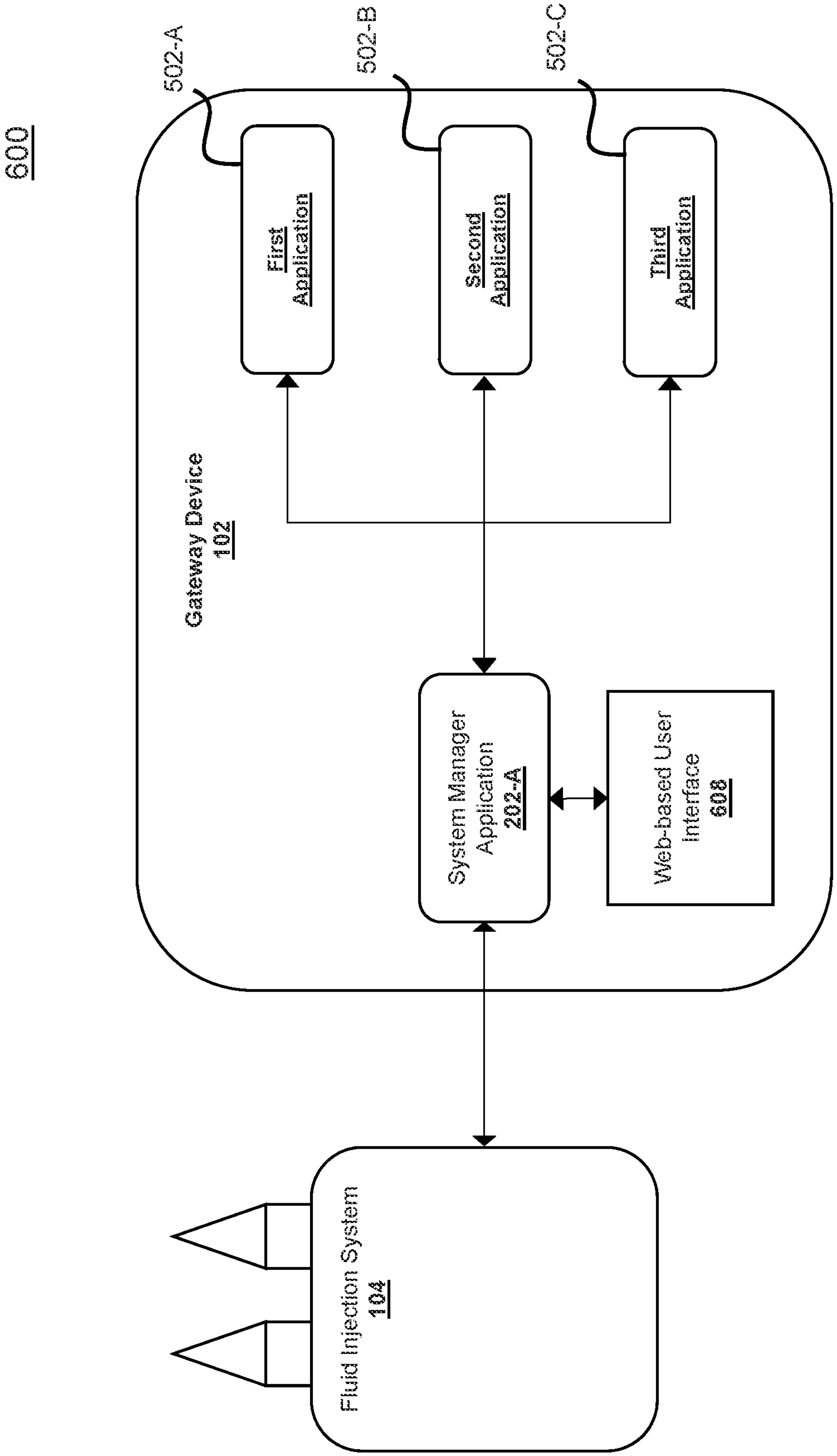
FIG. 6 is a diagram of a non-limiting embodiment of an implementation of a system for enabling communication between a fluid injection system and at least one of a plurality of external systems.

Referring now to FIG. 6, FIG. 6 is a diagram of a non-limiting embodiment of a system 600 for enabling communication between a fluid injection system and at least one of a plurality of external systems. In some non-limiting embodiments or aspects, one or more of the functions described herein with respect to system 600 may be performed (e.g., completely, partially, and/or the like) by gateway device 102. In some non-limiting embodiments, one or more of the functions described herein with respect to system 600 may be performed (e.g., completely, partially, and/or the like) by another device or a group of devices separate from and/or including gateway device 102, such as fluid injection system 104, hospital information system 106, medical imaging system 108, fluid injection system service and control system 110, and/or web server 112.

As shown in FIG. 6, first application 502-A (e.g., a first application of informatics application 202-B, fluid injection system service application 202-C, data management application 202-D, or imaging system connectivity application 202-E), second application 502-B (e.g., a second application of informatics application 202-B, fluid injection system service application 202-C, data management application 202-D, or imaging system connectivity application 202-E), and third application 502-C (e.g., a third application of informatics application 202-B, fluid injection system service application 202-C, data management application 202-D, or imaging system connectivity application 202-E) may be stored on gateway device 102. As further shown in FIG. 6, system manager application 202-A may provide for a selection of first application 502-A, second application 502-B, or third application 502-C based on web-based user interface 608 (e.g., based on web-based user interface 608 displayed on display unit 308) that is provided by system manager application 202-A. In some non-limiting embodiments, web-based user interface 608 may be served by web server 112 based on an API call to web server 112 from gateway device 102. As further shown in FIG. 6, gateway device 102 will provide a communication interface between the selected application and fluid injection system 104.

Figure 7:
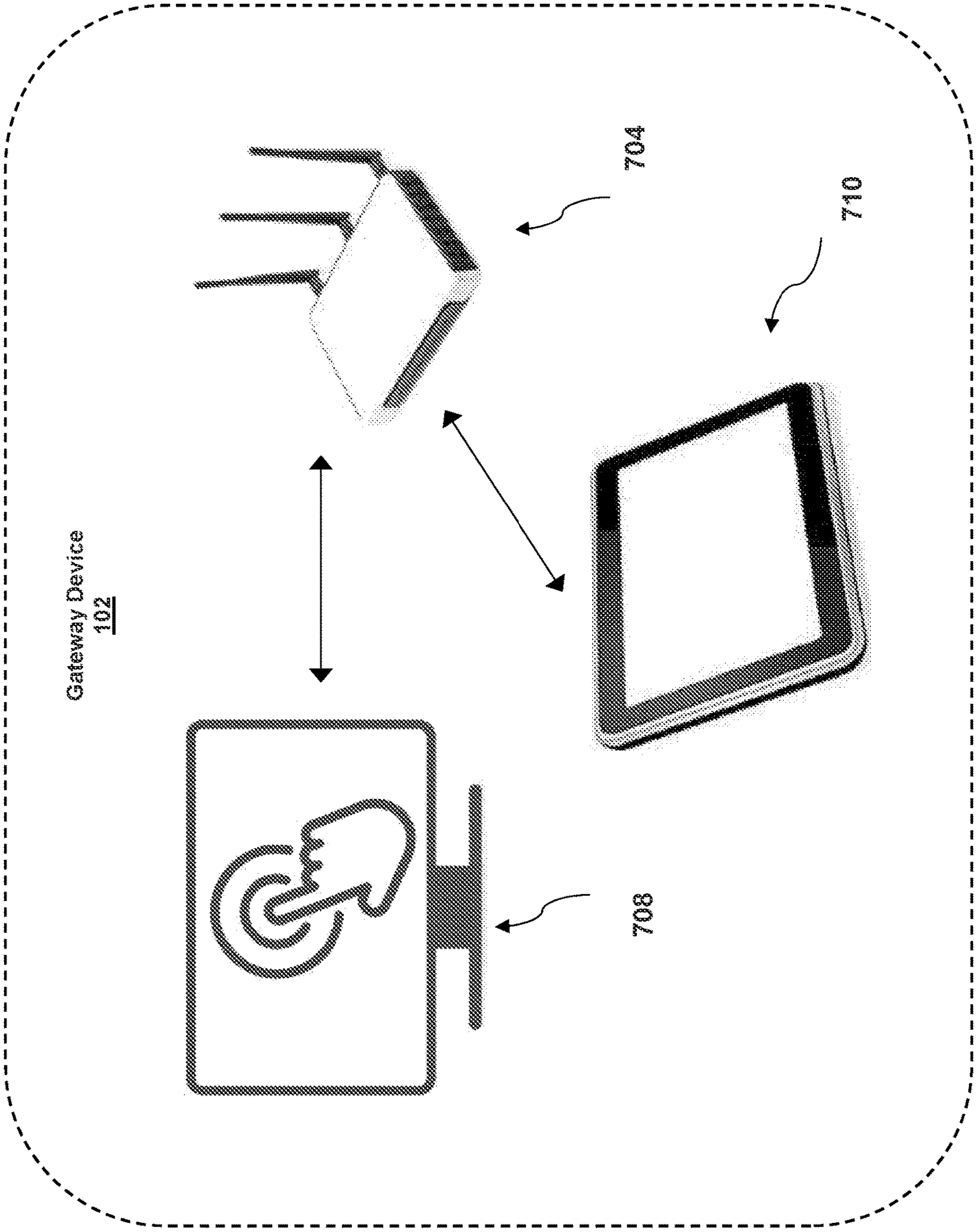
FIG. 7 is a diagram of a non-limiting embodiment of a gateway device.

Referring now to FIG. 7, FIG. 7 is a diagram of gateway device 102. As shown in FIG. 7, gateway device 102 includes display unit 708, display unit 710, and hub device 704. In some non-limiting embodiments, display unit 708 and/or display unit 710 may be the same as or similar to display unit 308. In some non-limiting embodiments, display unit 708 and/or display unit 710 may include a computing device, such as a portable computer (e.g., a laptop), a mobile device, and/or a touchscreen device (e.g., a computer with a touchscreen). In some non-limiting embodiments, hub device 704 may include a telecommunications gateway, such as a universal gateway. In some non-limiting embodiments, display unit 708 and/or display unit 710 may wirelessly interconnect with hub device 704. In some non-limiting embodiments, hub device 704 may include hardware components that allow hub device 704 to interconnect with fluid injection system 104, hospital information system 106, medical imaging system 108, fluid injection system service and control system 110, and/or web server 112. For example, hub device 704 may include one or more cellular modem modules, one or more Wi-Fi modules, one or more Bluetooth devices, and/or the like, to allow for wireless interconnections. Additionally or alternatively, hub device 704 may include one or more Ethernet cards, one or more Ethernet switches, one or more universal serial bus (USB) ports, and/or the like, to allow for wired interconnections.

Figure 8:
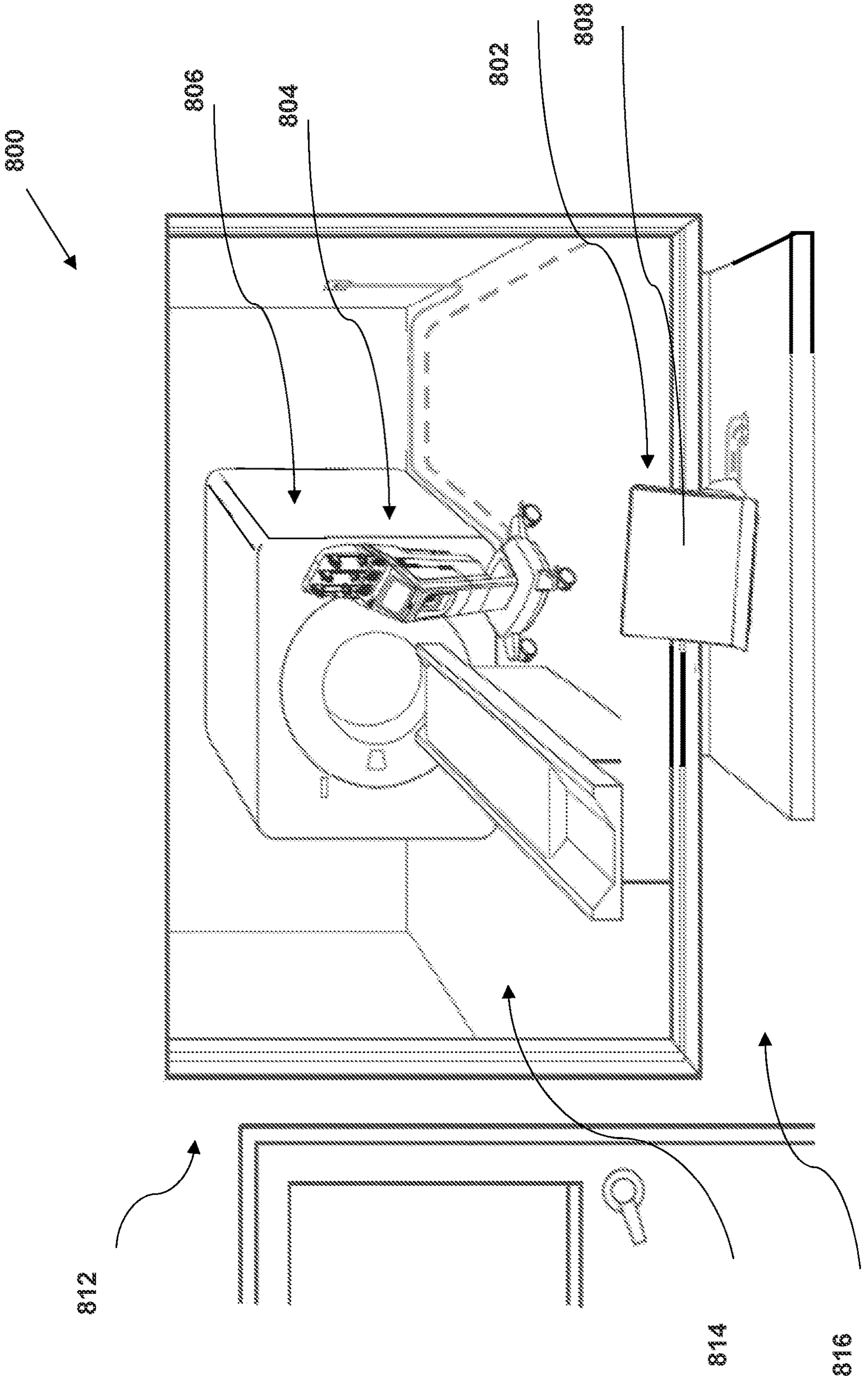
FIG. 8 illustrates an exemplary CT imaging suite in which is illustrated a non-limiting embodiment of an implementation of a fluid injection system and a gateway device.

Referring now to FIG. 8, FIG. 8 illustrates a non-limiting embodiment of an implementation 800 of fluid injector system 804, namely a multi-fluid delivery system, such as the MEDRAD® Centargo CT Injection System, medical imaging system 806, and gateway device 802, which includes display unit 808, located in computed tomography (CT) imaging suite 812. In some non-limiting embodiments, fluid injector 804 may be the same as or similar to fluid injection system 104, medical imaging system 806 may be the same as or similar to medical imaging system 108. In some non-limiting embodiments, gateway device 802 may be the same as or similar to gateway device 102 and display unit 808 may be the same as or similar to display unit 308 and/or display unit 708. As shown in FIG. 8, gateway device 802 may eliminate the need for a bifurcated fluid injection system that includes a scan room unit and a control room unit thereof located in scan room 814 and control room 816, respectively, of CT imaging suite 812. In non-limiting embodiments, gateway device 802 may provide a user interface (e.g., a web-based user interface) on display unit 808 for control of fluid injector system 804 and medical imaging system 806. In this way, gateway device 802 may eliminate the need for separate computing devices that are specifically designed for control of fluid injector system 804 and medical imaging system 808.

Figure 9:
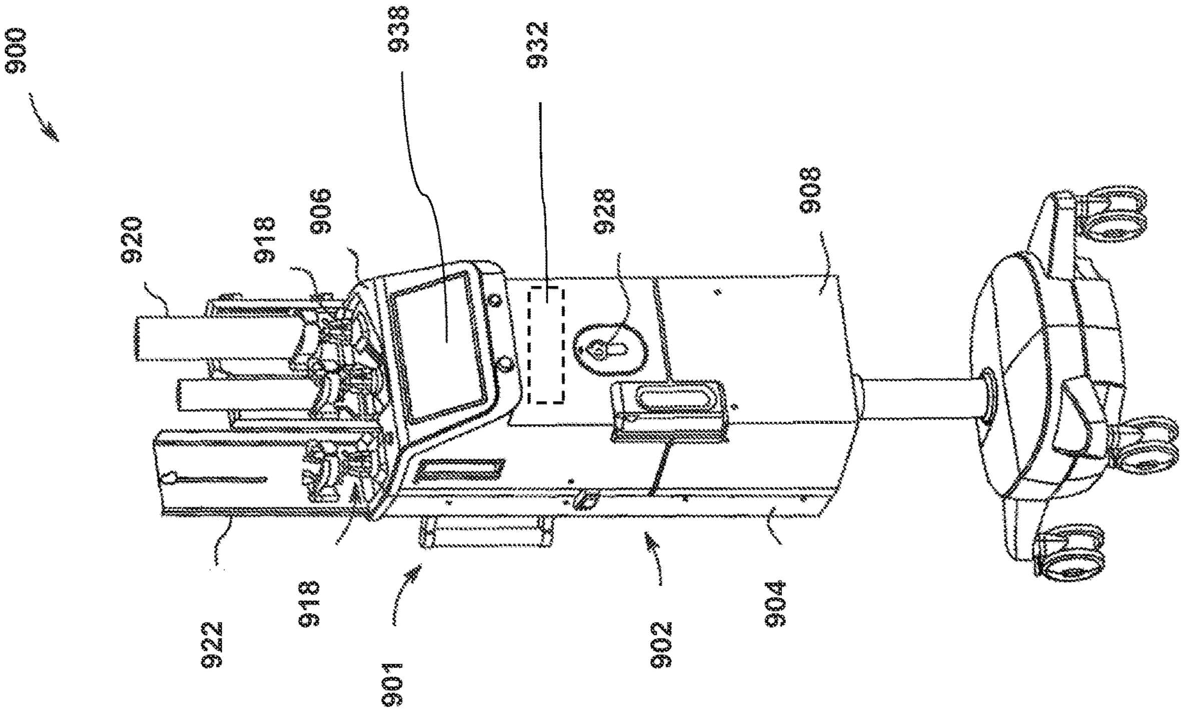
FIG. 9 illustrates a non-limiting embodiment of a fluid injection system that includes a gateway device.

Referring now to FIG. 9, FIG. 9 illustrates a non-limiting embodiment of fluid injector system 900, namely, a multi-fluid delivery system such as the MEDRAD® Centargo CT Injection System, with gateway device 932 and display unit 938. As shown in FIG. 9, fluid injector system 900 may be configured to (e.g., adapted to) provide feedback about compliance with usage instructions. In some non-limiting embodiments, fluid injector system 900 includes powered fluid injector 901 connected to a fluid delivery set intended to be associated with an injector device to deliver fluids from one or more single-dose or multi-dose containers and fluid path sets under pressure into a patient. In some non-limiting embodiments, powered fluid injector 901 includes injector housing 902 with opposed lateral sides 904, distal or upper end 906, and proximal or lower end 908. Injector housing 902 encloses the various mechanical drive components, electrical and power components necessary to drive the mechanical drive components, and control components, such as electronic memory and electronic control devices (hereinafter electronic control device(s)), used to control operation of reciprocally movable drive members, such as drive members associated with fluid injector system 900. Such drive members may be reciprocally operable via electro-mechanical drive components, such as a ball screw shaft driven by a motor, a voice coil actuator, a rack-and-pinion gear drive, a linear motor, and the like.

In some non-limiting embodiments, fluid injector system 900 may include at least one bulk fluid connector 918 for connection with at least one bulk fluid source 920. Alternatively, the fluid source could be a single dose vial, rather than a bulk source. In some examples or aspects, a plurality of bulk fluid connectors 918 may be provided. In some non-limiting embodiments, three bulk fluid connectors 918 may be provided in a side-by-side or other arrangement. In some non-limiting embodiments, at least one bulk fluid connector 918 may be a spike configured for removably connecting to the at least one bulk fluid source 920, such as a vial, bottle or a bag. The at least one bulk fluid connector 918 may have a reusable or non-reusable interface with each new bulk fluid source 920. The at least one bulk fluid connector 918 may be formed on or attached by tubing with the multi-patient disposable set, as described herein. The at least one bulk fluid source 920 may be configured for receiving a medical fluid, such as saline, an imaging contrast solution, or other medical fluid, for delivery to fluid injector system 900. Injector housing 902 may have at least one support member 922 for supporting the at least one bulk fluid source 920 once it is connected to fluid injector system 900. In some non-limiting embodiments, fluid injector system 900 may include connection port 928.

In some non-limiting embodiments, gateway device 932 may be the same as or similar to gateway device 102 and/or gateway device 802. In some non-limiting embodiments, display unit 938 may be the same as or similar to display unit 308, display unit 708, and/or display unit 808. As shown in FIG. 9, gateway device 932 and display unit 938 may be components of fluid injector system 900. For example, gateway device 932 may include a printed circuit board (PCB) that is installed within fluid injector system 900.

Figure 10:
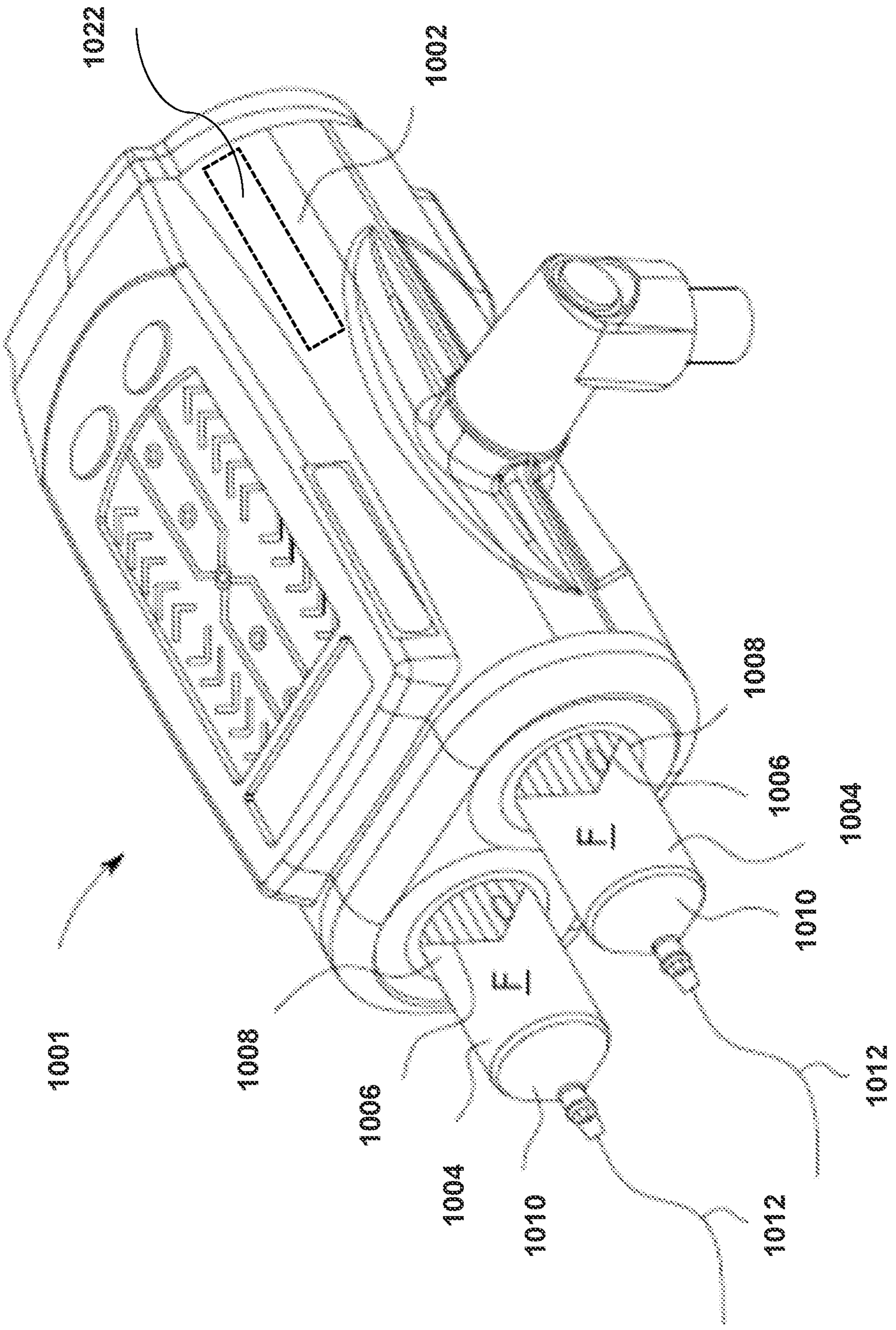
FIG. 10 illustrates a non-limiting embodiment of another fluid injection system that includes a gateway device.

Referring now to FIG. 10, FIG. 10 illustrates a non-limiting embodiment of injector head unit 1001 of a fluid injector system, such as the MEDRAD® Stellant Flex CT Injection System, with gateway device 1022. As shown in FIG. 10, injector head unit 1001 may include housing 1002 and at least one fluid reservoir 1004, such as a syringe or a fluid pump container. In some non-limiting embodiments, the fluid injection system may include a drive component to control fluid flow into or out of a fluid reservoir, such as a piston associated with each of fluid reservoirs 1004 that drive plungers 1006 within a barrel of fluid reservoir 1004. In some non-limiting embodiments, each of fluid reservoirs 1004 is adapted to releasably interface with housing 1002 at port 1008. Each fluid reservoir 1004 of the fluid injection system is configured to be filled with at least one medical fluid F, such as an imaging contrast media, saline solution, or any desired medical fluid. Each fluid reservoir 1004 may be filled with a different medical fluid F. In some non-limiting embodiments, the fluid injection system may be a multi-syringe injector, as shown, where two fluid reservoirs 1004 may be oriented side-by-side or in another spatial relationship and are separately actuated by respective pistons associated with the fluid injection system.

In some non-limiting embodiments, the fluid injection system may be used during a medical procedure to inject the at least one medical fluid F into the vasculature of a patient by driving plungers 1006 associated with fluid reservoir 1004 with a drive component. The drive component may move plunger 1006 toward distal end 1010 of fluid reservoir 1004 to expel the fluid F from fluid reservoir 1004 into and through fluid path set 1012 during a priming, purging, and/or fluid delivery step. In some non-limiting embodiments, fluid path set 1012 may include at least one tube or tube set configured to be in fluid communication with each fluid reservoir 1004 to place each fluid reservoir 1004 in fluid communication with a flexible administration tube and associated catheter for delivering the fluid F from each fluid reservoir 1004 to a patient at a vascular access site.

As shown in FIG. 10, gateway device 1022 may be a component of injector head unit 1001 of the fluid injector system. For example, gateway device 1022 may include a PCB that is installed within injector head unit 1001.

Although the above systems, methods, and computer program products have been described in detail for the purpose of illustration based on what is currently considered to be the most practical and preferred embodiments or aspects, it is to be understood that such detail is solely for that purpose and that the present disclosure is not limited to the described embodiments or aspects but, on the contrary, is intended to cover modifications and equivalent arrangements that are within the spirit and scope of the appended claims. For example, it is to be understood that the present disclosure contemplates that, to the extent possible, at least one feature of any embodiment or aspect can be combined with at least one feature of any other embodiment or aspect.

What is claimed is:

1. A system for enabling communication between a fluid injection system and at least one of a plurality of external systems, comprising:

a gateway device, the gateway device comprising:

at least one processor programmed or configured to:

provide a first communication interface between a hospital information system and the fluid injection system;

provide a second communication interface between a fluid injection system service and control system associated with the fluid injection system and the fluid injection system; and provide a third communication interface between a medical imaging system and the fluid injection system;

a memory device, the memory device storing a plurality of applications that perform a set of functionalities on an application programming interface (API) that allows data to be sent to an external system associated with the API via the gateway device and allows data to be received from the external system associated with the API via the gateway device, and wherein the plurality of applications comprises:

an informatics application associated with the first communication interface between the hospital information system and the fluid injection system, wherein the fluid injection system receives data based on an API call via the informatics application from the fluid injection system to the gateway device, wherein the informatics application comprises at least one of the following:

a patient procedure tracking service, wherein the patient procedure tracking service provides reporting, alerts, and/or messaging with regard to timing of patient procedures, an image archive and communication service, wherein the image archive and communication service provides receiving, storing, accessing, and/or transmitting with regards to images, a radiology information service, wherein the radiology information service provides patient scheduling, resource management, examination performance tracking, reporting, results distribution, and/or procedure billing with regard to medical imaging procedures, a radiology analytics service, wherein the radiology analytics service provides reporting, tracking, alerts, and/or messaging with regard to information associated with a medical imaging procedure, a fluid injector management service, wherein the fluid injector management service provides receiving, storing, transmitting, and/or otherwise managing fluid injection systems and/or fluid injection protocols used by the fluid injection systems, a data insights service, wherein the data insights service provides reporting, tracking, alerts, and/or messaging with regard to equipment and/or services used during medical imaging procedures, and any combination thereof;

a data management application associated with the first communication interface between the hospital information system and the fluid injection system, wherein the data management application manages file system and database operations of the gateway device and controls storage of data for the fluid injection system, wherein the data management application comprises at least one of the following:

a file system management service, wherein the file system management service manages a file system of the gateway device, a database management service, wherein the database management service manages one or more databases associated with the gateway device, and any combination thereof;

a fluid injection system service application associated with the second communication interface between the fluid injection system service and control system associated with the fluid injection system and the fluid injection system, wherein the remote service connectivity fluid injection system service application comprises at least one of the following:

a remote service connectivity service, wherein the remote service connectivity service provides access to and/or control of diagnostic operations of fluid injection system by a remote service technician, an upgrade repository service, wherein the upgrade repository service provides receiving, storing, and/or accessing with regard to records regarding upgrades for services of the gateway device, a licenses management service, wherein the licenses management service provides receiving, storing, and/or accessing with regard to records regarding licenses for services of the gateway device and or the fluid injection system, a periodic data management service, wherein the periodic data management service provides reporting, tracking, alerts, and/or messaging with regard to time sensitive data associated with the gateway device and/or the fluid injection system, and any combination thereof;

an imaging connectivity system application associated with the third communication interface between the medical imaging system and the fluid injection system, wherein the fluid injection system communicates with the medical imaging system via the imaging connectivity system application, wherein the imaging connectivity system application comprises an imaging system interface, wherein the imaging system interface comprises an interface of the medical imaging system that is generated in a standard format and utilized by the fluid injection system for communication with the medical imaging system to; and a system manager application that provides a web-based user interface, wherein the fluid injection system receives a selection of an application of the plurality of applications via the web-based user interface provided by the system manager application, wherein the web-based user interface is displayed on a display unit and is served by a web server based on an API call via the system manager application to the web server, and wherein a communication interface is provided between a selected application and the fluid injection system via the system manager application, wherein the system manager application comprises at least one of the following:

a network management service, wherein the network management service provides control of network addresses and/or communication protocols, an upgrade management service, wherein the upgrade management service provides control regarding upgrades to be made to services of the informatics application, a security management service, wherein the security management service provides control regarding users that are able to access the gateway device and/or authentication methods for access to the gateway device, a container management service, wherein the container management service provides for functionality associated with control of services, and any combination thereof.

2. The system of claim 1, wherein the at least one processor is further programmed or configured to:

transmit data associated with informatics received from the hospital information system to the fluid injection system via a communication network based on an application programming interface (API) call from the fluid injection system.

3. The system of claim 2, wherein the at least one processor is further programmed or configured to: receive the data associated with informatics from the hospital information system via the communication network according to a communications protocol for communicating the data associated with informatics.

4. The system of claim 3, wherein, when receiving the data associated with informatics from the hospital information system, the at least one processor is programmed or configured to: receive data associated with a patient procedure from the hospital information system via the communication network according to a Digital Imaging and Communications in Medicine (DICOM) communications protocol.

5. The system of claim 3, wherein, when receiving the data associated with informatics from the hospital information system, the at least one processor is programmed or configured to: receive data associated with an operation of the fluid injection system from the hospital information system via the communication network based on an API call.

6. The system of claim 3, wherein, when receiving the data associated with informatics from the hospital information system, the at least one processor is programmed or configured to: receive data associated with a radiology image from the hospital information system via the communication network according to a Digital Imaging and Communications in Medicine (DICOM) communications protocol.

7. The system of claim 3, wherein, when receiving the data associated with informatics from the hospital information system, the at least one processor is programmed or configured to: receive data associated with a radiology procedure from the hospital information system via the communication network according to a Health Level Seven (HL7) standard communications protocol.

8. The system of claim 3, wherein, when receiving the data associated with informatics from the hospital information system, the at least one processor is programmed or configured to: receive data associated with radiation dosage during a radiology imaging study from the hospital information system via the communication network based on an API call.

9. The system of claim 3, wherein the at least one processor is further programmed or configured to:

receive data associated with a service function of the fluid injection system from the fluid injection system service and control system via the communication network based on an API call.

10. The system of claim 3, wherein the at least one processor is further programmed or configured to: receive data associated with an operation of the medical imaging system from the medical imaging system via the communication network based on an API call.

11. The system of claim 1, wherein the at least one processor is further programmed or configured to: transmit data associated with service information received from the fluid injection system service and control system to the fluid injection system via a communication network based on an API call from the fluid injection system.

12. The system of claim 1, wherein the at least one processor is further programmed or configured to: transmit data associated with an image received from the medical imaging system to the fluid injection system via a communication network based on an API call from the fluid injection system.

13. The system of claim 1, wherein the at least one processor is further programmed or configured to: provide a graphical user interface to a user to receive a user input.

14. The system of claim 1, wherein the gateway device comprises a universal gateway.

15. A system for enabling communication between a fluid injection system and at least one of a plurality of external systems, comprising:

a fluid injection system; and a gateway device, the gateway device comprising:

at least one processor programmed or configured to:

provide a first communication interface between a hospital information system and the fluid injection system;

provide a second communication interface between the fluid injection system service and control system associated with the fluid injection system and the fluid injection system; and provide a third communication interface between a medical imaging system and the fluid injection system; and a memory device, the memory device storing a plurality of applications that perform a set of functionalities on an application programming interface (API) that allows data to be sent to an external system associated with the API via the gateway device and allows data to be received from the external system associated with the API via the gateway device, and wherein the plurality of applications comprises:

an informatics application associated with the first communication interface between the hospital information system and the fluid injection system, wherein the fluid injection system receives data based on an API call via the informatics application from the fluid injection system to the gateway device, wherein the informatics application comprises at least one of the following:

a patient procedure tracking service, wherein the patient procedure tracking service provides reporting, alerts, and/or messaging with regard to timing of patient procedures, an image archive and communication service, wherein the image archive and communication service provides receiving, storing, accessing, and/or transmitting with regards to images, a radiology information service, wherein the radiology information service provides patient scheduling, resource management, examination performance tracking, reporting, results distribution, and/or procedure billing with regard to medical imaging procedures, a radiology analytics service, wherein the radiology analytics service provides reporting, tracking, alerts, and/or messaging with regard to information associated with a medical imaging procedure, a fluid injector management service, wherein the fluid injector management service provides receiving, storing, transmitting, and/or otherwise managing fluid injection systems and/or fluid injection protocols used by the fluid injection systems, a data insights service, wherein the data insights service provides reporting, tracking, alerts, and/or messaging with regard to equipment and/or services used during medical imaging procedures, and any combination thereof;

a data management application associated with the first communication interface between the hospital information system and the fluid injection system, wherein the data management application manages file system and database operations of the gateway device and controls storage of data for the fluid injection system, wherein the data management application comprises at least one of the following:

a file system management service, wherein the file system management service manages a file system of the gateway device, a database management service, wherein the database management service manages one or more databases associated with the gateway device, and any combination thereof;

a fluid injection system service application associated with the second communication interface between the fluid injection system service and control system associated with the fluid injection system and the fluid injection system, wherein the fluid injection system service application comprises at least one of the following:

a remote service connectivity service, wherein the remote service connectivity service provides access to and/or control of diagnostic operations of fluid injection system by a remote service technician, an upgrade repository service, wherein the upgrade repository service provides receiving, storing, and/or accessing with regard to records regarding upgrades for services of the gateway device, a licenses management service, wherein the licenses management service provides receiving, storing, and/or accessing with regard to records regarding licenses for services of the gateway device and or the fluid injection system, a periodic data management service, wherein the periodic data management service provides reporting, tracking, alerts, and/or messaging with regard to time sensitive data associated with the gateway device and/or the fluid injection system, and any combination thereof;

an imaging connectivity system application associated with the third communication interface between the medical imaging system and the fluid injection system, wherein the fluid injection system communicates with the medical imaging system via the imaging connectivity system application wherein the imaging connectivity system application comprises an imaging system interface, wherein the imaging system interface comprises an interface of the medical imaging system that is generated in a standard format and utilized by the fluid injection system for communication with the medical imaging system; and a system manager application that provides a web-based user interface, wherein the fluid injection system receives a selection of an application of the plurality of applications via the web-based user interface provided by the system manager application, wherein the web-based user interface is displayed on a display unit and is served by a web server based on an API call via the system manager application to the web server, and wherein a communication interface is provided between a selected application and the fluid injection system via the system manager application, wherein the system manager application comprises at least one of the following:

a network management service, wherein the network management service provides control of network addresses and/or communication protocols, an upgrade management service, wherein the upgrade management service provides control regarding upgrades to be made to services of the informatics application, a security management service, wherein the security management service provides control regarding users that are able to access the gateway device and/or authentication methods for access to the gateway device, a container management service, wherein the container management service provides for functionality associated with control of services, and any combination thereof.

16. The system of claim 15, wherein the at least one processor is further programmed or configured to:

transmit data associated with informatics received from the hospital information system to the fluid injection system via a communication network based on an application programming interface (API) call from the fluid injection system.

17. The system of claim 16, wherein the at least one processor is further programmed or configured to: receive the data associated with informatics from the hospital information system via the communication network according to a communications protocol for communicating the data associated with informatics.

18. The system of claim 17, wherein, when receiving the data associated with informatics from the hospital information system, the at least one processor is programmed or configured to: receive data associated with a patient procedure from the hospital information system via the communication network according to a Digital Imaging and Communications in Medicine (DICOM) communications protocol.

19. The system of claim 17, wherein, when receiving the data associated with informatics from the hospital information system, the at least one processor is programmed or configured to: receive data associated with an operation of the fluid injection system from the hospital information system via the communication network based on an API call.

20. The system of claim 17, wherein, when receiving the data associated with informatics from the hospital information system, the at least one processor is programmed or configured to: receive data associated with a radiology image from the hospital information system via the communication network according to a Digital Imaging and Communications in Medicine (DICOM) communications protocol.

21. The system of claim 17, wherein when receiving the data associated with informatics from the hospital information system, the at least one processor is programmed or configured to: receive data associated with a radiology procedure from the hospital information system via the communication network according to a Health Level Seven (HL7) standard communications protocol.

22. The system of claim 17, wherein, when receiving the data associated with informatics from the hospital information system, the at least one processor is programmed or configured to:

receive data associated with radiation dosage during a radiology imaging study from the hospital information system via the communication network based on an API call.

23. The system of claim 17, wherein the at least one processor is further programmed or configured to:

receive data associated with a service function of the fluid injection system from the fluid injection system service and control system via the communication network based on an API call.

24. The system of claim 17, wherein the at least one processor is further programmed or configured to: receive data associated with an operation of the medical imaging system from the medical imaging system via the communications network based on an API call.

25. The system of claim 15, wherein the at least one processor is further programmed or configured to: transmit data associated with service information received from the fluid injection system service and control system to the fluid injection system via a communication network based on an API call from the fluid injection system.

26. The system of claim 15, wherein the at least one processor is further programmed or configured to: transmit data associated with an image received from the medical imaging system to the fluid injection system via a communications network based on an API call from the fluid injection system.

27. The system of claim 15, wherein the at least one processor is further programmed or configured to: provide a graphical user interface to a user to receive a user input.

28. The system of claim 15, wherein the gateway device comprises a universal gateway.

* * * * *